United States Patent
Briman et al.

(10) Patent No.: US 9,234,867 B2
(45) Date of Patent: Jan. 12, 2016

(54) ELECTROCHEMICAL NANOSENSORS FOR BIOMOLECULE DETECTION

(71) Applicant: Nanomix, Inc., Emeryville, CA (US)

(72) Inventors: Mikhail Briman, Emeryville, CA (US); Ray Radtkey, Oakland, CA (US); Eugene Tu, San Diego, CA (US); Christian Valcke, Orinda, CA (US)

(73) Assignee: Nanomix, Inc., Emeryville, CA (US)

( * ) Notice: Subject to any disclaimer, the term of this patent is extended or adjusted under 35 U.S.C. 154(b) by 0 days.

(21) Appl. No.: 13/867,925

(22) Filed: Apr. 22, 2013

(65) Prior Publication Data

US 2013/0306491 A1 Nov. 21, 2013

Related U.S. Application Data

(63) Continuation of application No. 11/868,373, filed on Oct. 5, 2007, now Pat. No. 8,425,745.

(60) Provisional application No. 60/850,217, filed on Oct. 6, 2006, provisional application No. 60/901,538, filed on Feb. 14, 2007.

(51) Int. Cl.
*G01N 27/327* (2006.01)
*G01N 33/543* (2006.01)

(52) U.S. Cl.
CPC ........ *G01N 27/3278* (2013.01); *G01N 33/5438* (2013.01)

(58) Field of Classification Search
CPC ............ G01N 33/566; G01N 33/5438; G01N 33/543; G01N 33/54353; G01N 33/53; G01N 33/54386; G01N 33/58; G01N 33/581; G01N 33/6857; G01N 33/5302; G01N 33/536; G01N 2021/6441

USPC .................. 205/777.5, 792; 435/6.1, 6.9, 7.1, 435/7.7–7.72, 7.9–7.95; 436/512, 528–535, 436/538, 149–150

See application file for complete search history.

(56) References Cited

U.S. PATENT DOCUMENTS

| | | |
|---|---|---|
| 4,851,195 A | 7/1989 | Matthews et al. |
| 4,935,345 A | 6/1990 | Guilbeau et al. |

(Continued)

FOREIGN PATENT DOCUMENTS

| | | |
|---|---|---|
| WO | 02/15240 | 2/2002 |
| WO | 2008/045799 | 4/2008 |
| WO | 2009/017911 | 2/2009 |

OTHER PUBLICATIONS

T.J. Davies, et al. "Nanotrench Arrays Reveal Insight into Graphite Electrochemistry" Angewandt Chemie, vol. 117, 2005, p. 5251-5256.*

(Continued)

*Primary Examiner* — J. Christopher Ball
(74) *Attorney, Agent, or Firm* — Weaver Austin Villeneuve & Sampson LLP

(57) ABSTRACT

Sensor devices, methods and kits for detection of biomolecules are provided. According to various embodiments, the devices, methods and kits provide enhanced sensitivity through the measurement of electrochemical impedance and related properties. Certain embodiments employ nanostructured electrode elements including nanotubes, nanoparticles, nanowires, and nanocones. In a particular embodiment, single walled carbon nanotubes disposed in interconnected networks are used as electrodes. The device, methods and kits described herein have application for detection and measurement of biomolecular species including polynucleotides, proteins, polysaccharides and the like.

17 Claims, 16 Drawing Sheets

(56) References Cited

U.S. PATENT DOCUMENTS

| | | | |
|---|---|---|---|
| 5,246,859 | A | 9/1993 | Nelson et al. |
| 5,382,417 | A | 1/1995 | Haase |
| 5,571,401 | A | 11/1996 | Lewis et al. |
| 5,736,188 | A | 4/1998 | Alcock et al. |
| 6,217,828 | B1 | 4/2001 | Bretscher et al. |
| 6,465,132 | B1 | 10/2002 | Jin |
| 6,489,394 | B1 | 12/2002 | Andros |
| 6,528,020 | B1 | 3/2003 | Dai et al. |
| 6,797,325 | B2 | 9/2004 | Wang et al. |
| 6,962,823 | B2 | 11/2005 | Empedocles et al. |
| 7,955,559 | B2 | 6/2011 | Joshi et al. |
| 8,425,745 | B2 | 4/2013 | Briman et al. |
| 8,778,269 | B2 | 7/2014 | Joshi et al. |
| 8,900,517 | B2 | 12/2014 | Gabriel et al. |
| 2002/0117659 | A1 | 8/2002 | Lieber et al. |
| 2002/0130333 | A1 | 9/2002 | Watanabe et al. |
| 2003/0040173 | A1 | 2/2003 | Fonash et al. |
| 2003/0041438 | A1 | 3/2003 | Wei et al. |
| 2003/0077642 | A1* | 4/2003 | Fritsch et al. .............. 435/6 |
| 2003/0113713 | A1 | 6/2003 | Glezer et al. |
| 2003/0134433 | A1 | 7/2003 | Gabriel et al. |
| 2003/0186167 | A1 | 10/2003 | Johnson, Jr. et al. |
| 2004/0018587 | A1 | 1/2004 | Makowski et al. |
| 2004/0023428 | A1 | 2/2004 | Gole et al. |
| 2004/0065970 | A1 | 4/2004 | Blanchet-Fincher |
| 2004/0067646 | A1 | 4/2004 | Tao et al. |
| 2004/0091285 | A1 | 5/2004 | Lewis |
| 2004/0120183 | A1 | 6/2004 | Appenzeller et al. |
| 2004/0146958 | A1 | 7/2004 | Bae et al. |
| 2004/0158410 | A1 | 8/2004 | Ono et al. |
| 2004/0200734 | A1 | 10/2004 | Co et al. |
| 2004/0259180 | A1 | 12/2004 | Burke et al. |
| 2005/0186333 | A1 | 8/2005 | Douglas |
| 2005/0230270 | A1 | 10/2005 | Ren et al. |
| 2006/0040381 | A1 | 2/2006 | Zhao et al. |
| 2006/0115640 | A1 | 6/2006 | Yodh et al. |
| 2006/0141469 | A1 | 6/2006 | Rossier et al. |
| 2007/0208243 | A1 | 9/2007 | Gabriel et al. |
| 2008/0185295 | A1 | 8/2008 | Briman et al. |
| 2009/0084678 | A1 | 4/2009 | Joshi et al. |
| 2011/0003698 | A1 | 1/2011 | Gabriel et al. |
| 2012/0018301 | A1 | 1/2012 | Joshi et al. |
| 2013/0306491 | A1 | 11/2013 | Briman et al. |
| 2014/0353154 | A1 | 12/2014 | Joshi et al. |

OTHER PUBLICATIONS

U.S. Appl. No. 14/558,675, filed Dec. 2, 2014, Gabriel et al.
US Office Action dated Jun. 6, 2011 issued in U.S. Appl. No. 11/868,373.
US Final Office Action dated Feb. 6, 2012 issued in U.S. Appl. No. 11/868,373.
US Notice of Allowance dated Aug. 31, 2012 issued in U.S. Appl. No. 11/868,373.
US Notice of Allowance dated Dec. 21, 2012 issued in U.S. Appl. No. 11/868,373.
US Office Action dated Apr. 29, 2011 issued in U.S. Appl. No. 11/938,180.
US Final Office Action dated Jan. 10, 2012 issued in U.S. Appl. No. 11/938,180.
US Office Action dated Nov. 29, 2012 issued in U.S. Appl. No. 11/938,180.
US Final Office Action dated Sep. 12, 2013 issued in U.S. Appl. No. 11/938,180.
US Notice of Allowance dated Mar. 31, 2014 issued in U.S. Appl. No. 11/938,180.
US Notice of Allowance dated Jul. 21, 2014 issued in U.S. Appl. No. 11/938,180.
US Office Action dated Feb. 25, 2008 issued in U.S. Appl. No. 11/274,747.
US Examiner Interview Summary dated May 28, 2008 issued in U.S. Appl. No. 11/274,747.
US Office Action Final dated Feb. 11, 2009 issued in U.S. Appl. No. 11/274,747.
US Notice of Abandonment dated Sep. 11, 2009 issued in U.S. Appl. No. 11/274,747.
US Office Action dated May 28, 2010 issued in U.S. Appl. No. 12/146,320.
US Notice of Allowance dated Dec. 3, 2010 issued in U.S. Appl. No. 12/146,320.
US Notice of Allowance dated Jan. 25, 2011 issued in U.S. Appl. No. 12/146,320.
US Office Action dated Jan. 25, 2013 issued in U.S. Appl. No. 13/092,869.
US Final Office Action dated Aug. 8, 2013 issued in U.S. Appl. No. 13/092,869.
US Notice of Allowance dated Dec. 10, 2013 issued in U.S. Appl. No. 13/092,869.
PCT International Search Report dated Sep. 9, 2008 issued in PCT/US07/080603.
PCT International Preliminary Report on Patentability and Written Opinion dated Apr. 7, 2009 issued in PCT/US07/080603.
PCT International Search Report dated Jan. 2, 2009 issued in PCT/US2008/68228.
PCT International Preliminary Report on Patentability and Written Opinion dated Jan. 5, 2010 issued in PCT/US2008/68228.
Ong et al., "A Carbon Nanotube-based Sensor for C02 Monitoring," *Sensors*, vol. 1, pp. 193-205; published Nov. 2, 2001.
Zhao et al., (Jan. 2004) "Synthesis and Properties of a Water-Soluble Single-Walled Carbon Nanotube-Poly(*m*-aminobenzene sulfonic acid) Graft Copolymer", *Adv. Funct. Mater.* 14(1):71-76.

* cited by examiner

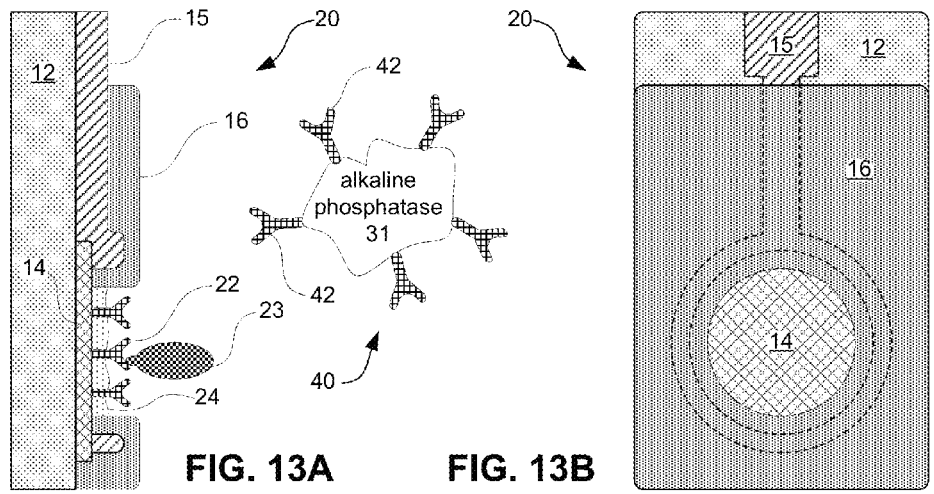
FIG. 13A   FIG. 13B
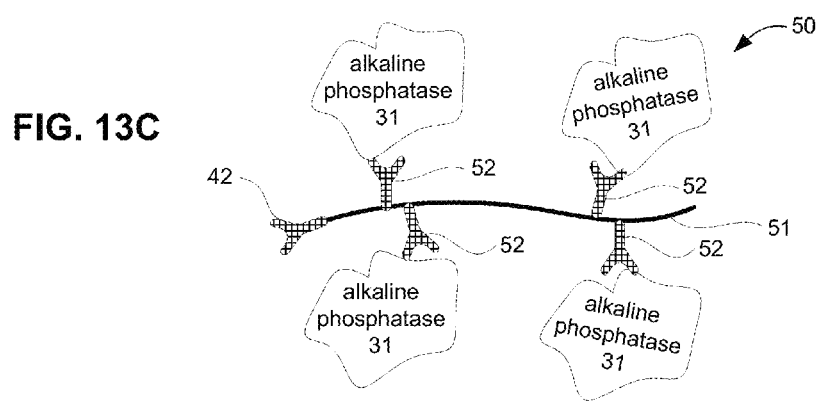
FIG. 13C
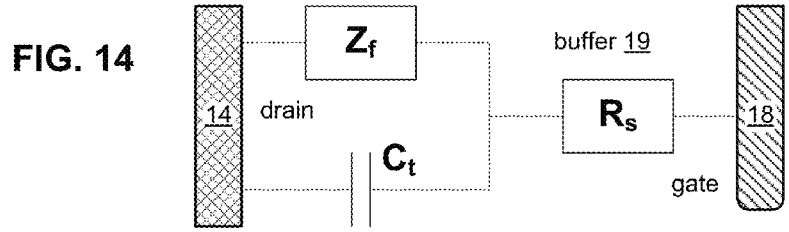
FIG. 14

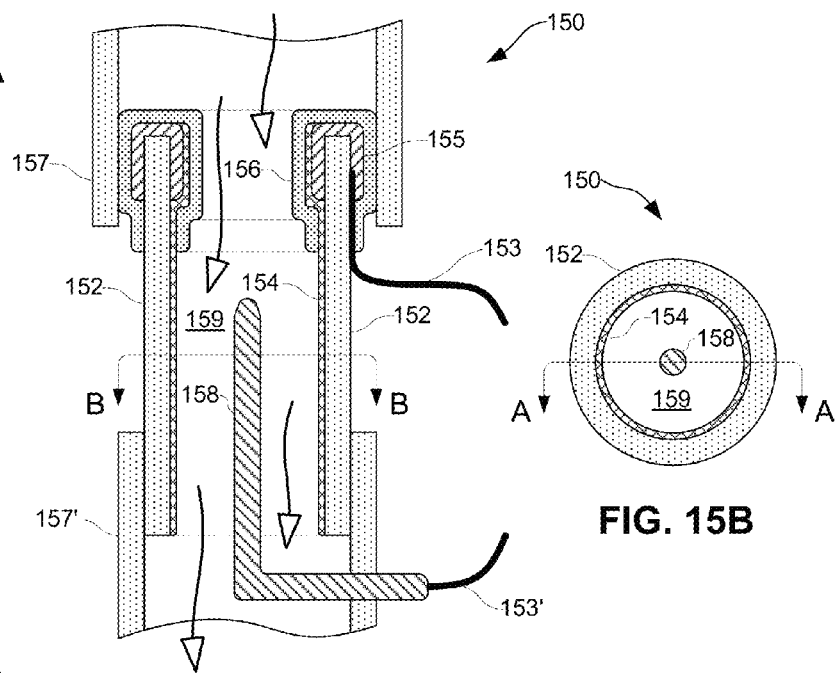
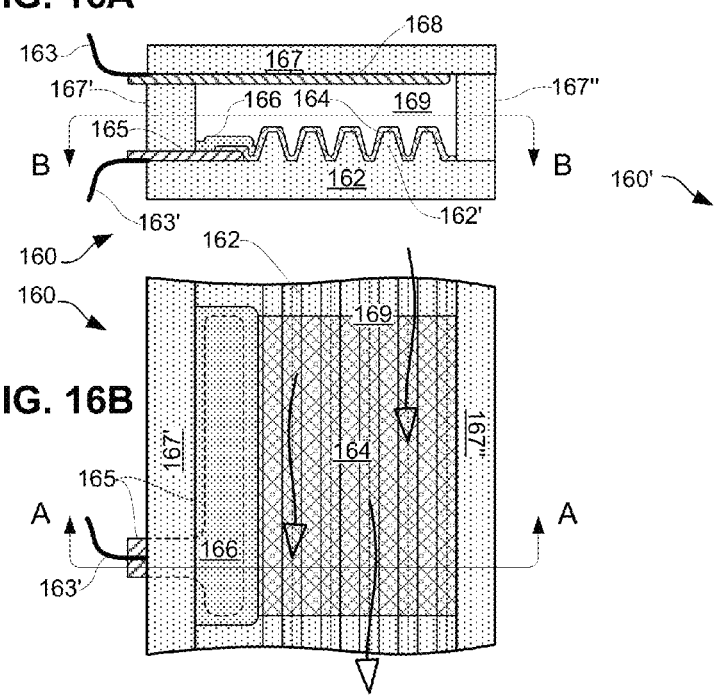
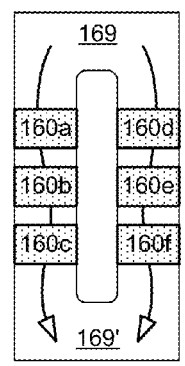

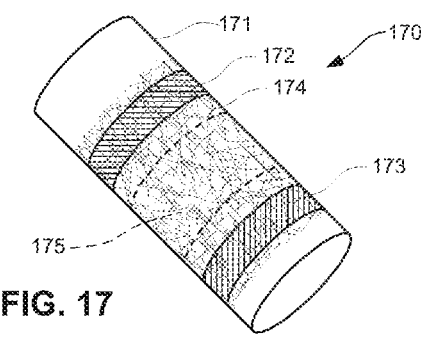
FIG. 17
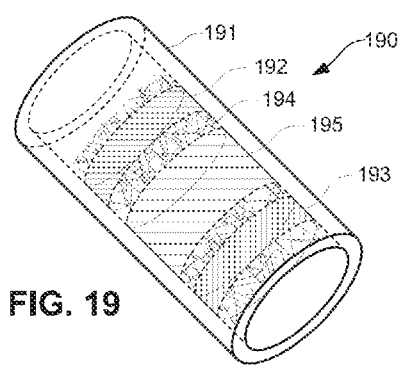
FIG. 19
FIGS. 18A-18H
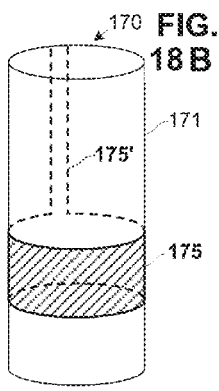
FIG. 18A  FIG. 18B
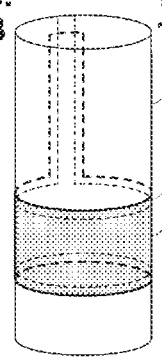
FIG. 18C
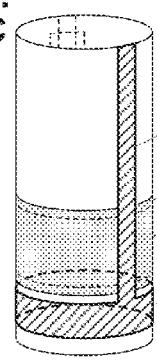
FIG. 18D
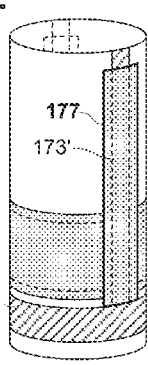
FIG. 18E  FIG. 18F
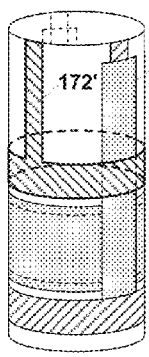
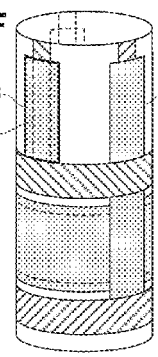
FIG. 18G
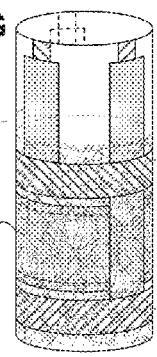
FIG. 18H
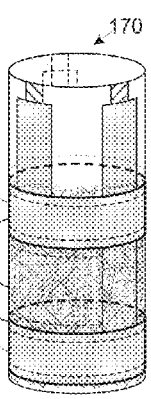

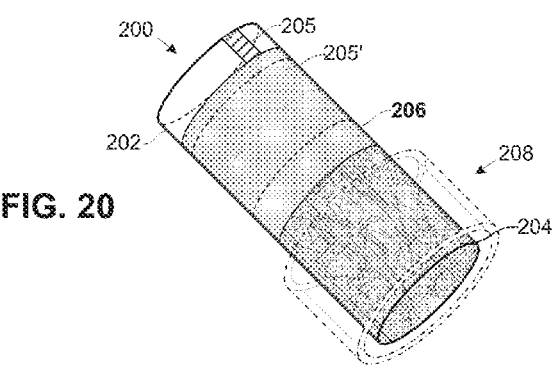
FIG. 20
FIGS. 21A-21F
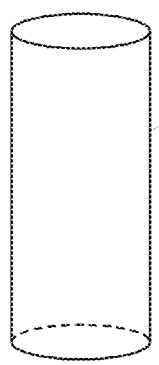
FIG. 21A
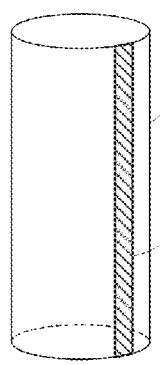
FIG. 21B
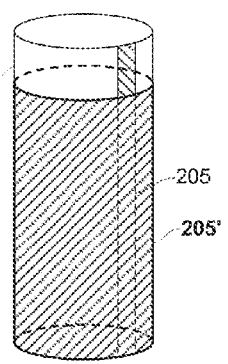
FIG. 21C
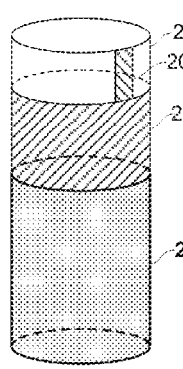
FIG. 21D
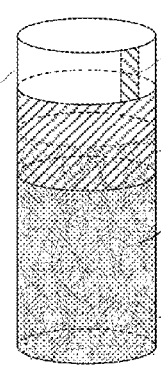
FIG. 21E
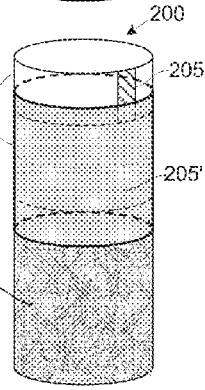
FIG. 21F

FIG. 29
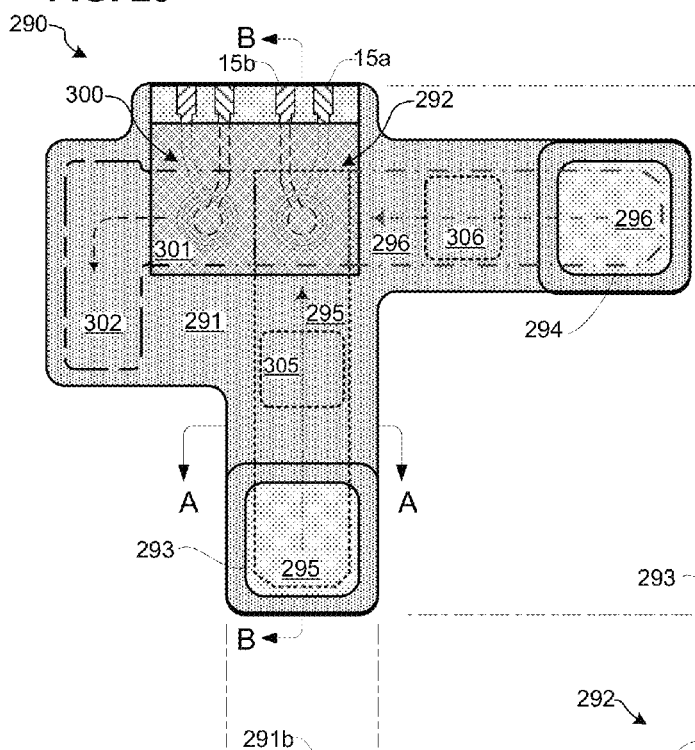
FIG. 29A
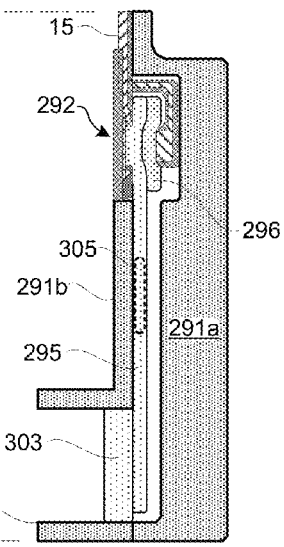
FIG. 29B
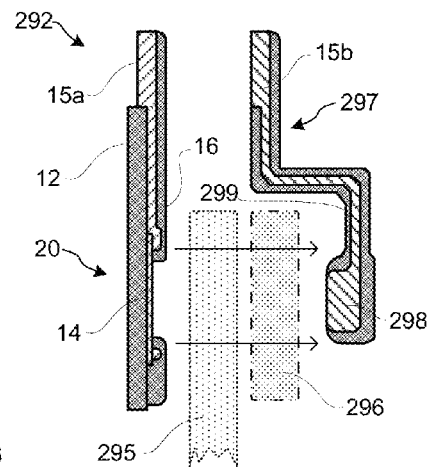
FIG. 29C
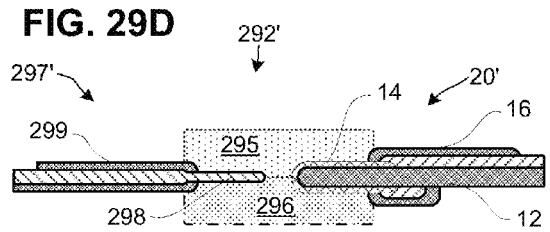
FIG. 29D

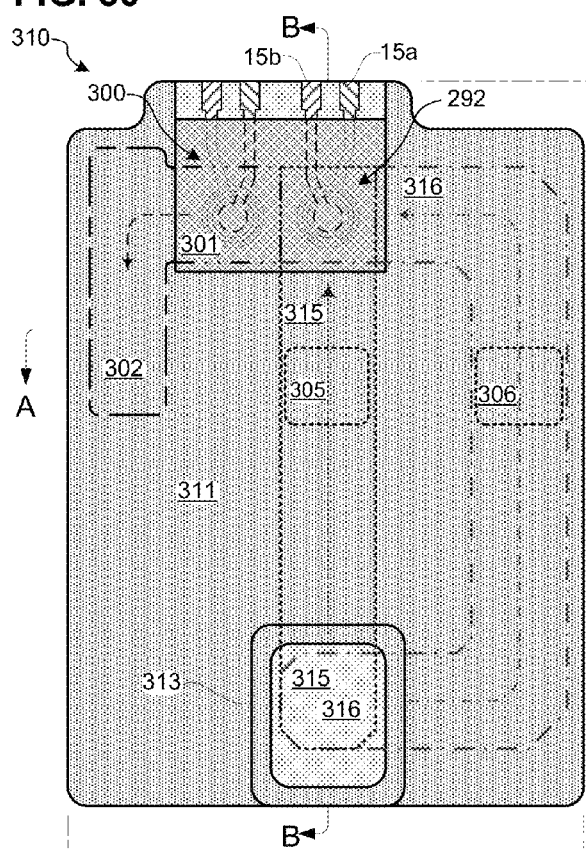
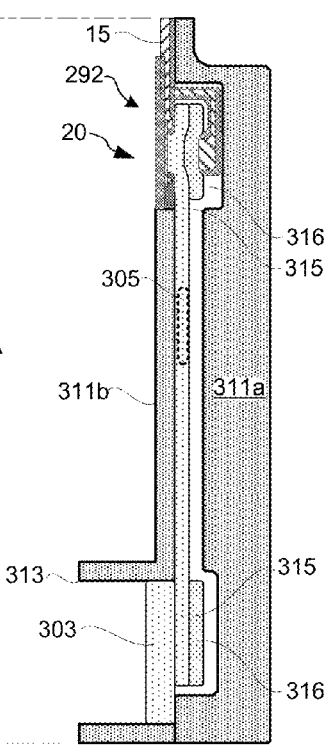
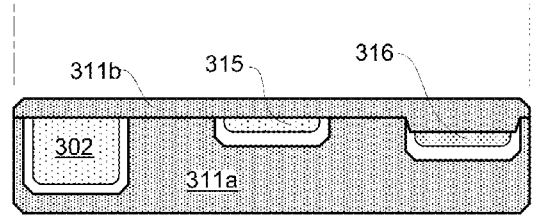
FIG. 30
FIG. 30B
FIG. 30A

ELECTROCHEMICAL NANOSENSORS FOR BIOMOLECULE DETECTION

CROSS-REFERENCE TO RELATED APPLICATIONS

This application is a continuation of and claims priority to U.S. application Ser. No. 11/868,373, (to issue as U.S. Pat. No. 8,425,745 on Apr. 23, 2013) which claims the benefit of priority under 35 USC. §119(e) to U.S. Provisional Applications Nos. 60/850,217, filed Oct. 6, 2006, entitled "Electrochemical nanosensors for biomolecule detection"; and 60/901,538, filed Feb. 14, 2007, entitled "Electrochemical nanosensors for biomolecule detection," all of which are incorporated herein by this reference for all purposes.

Each of the following patent applications is incorporated by this reference in its entirety for all purposes and relates to the present application in some manner:

International Application No. PCT/US05/047,143 filed Dec. 23, 2005 (published WO2006-071,895), entitled "Nanoelectronic sensor devices for DNA detection and recognition of polynucleotide sequences;"

U.S. application Ser. No. 11/636,360 filed Dec. 8, 2006 (now U.S. Pat. No. 8,152,991), entitled "Ammonia Nanosensors, And Environmental Control System";

U.S. application Ser. No. 11/274,747 filed Nov. 14, 2006 (published 2007-0208,243) entitled "Nanoelectronic Glucose Sensors;"

U.S. application Ser. No. 10/846,072 filed May 14, 2004 (now U.S. Pat. No. 7,956,525), entitled "Flexible nanotube transistors;" and U.S. application Ser. No. 11/703,293 filed Feb. 7, 2007 (published 2007-0140946) entitled "Dispersed Growth of Nanotubes on A Substrate."

BACKGROUND

Successful DNA detection has been demonstrated by coinventors herein, for example using nanoelectronic field effect transistor sensors including carbon nanotube networks (NTFET) functionalized with oligonucleotide probes. See A Star, E Tu, J Niemann, J-C P Gabriel, C S Joiner, and C Valcke, "*Label-free detection of DNA hybridization using carbon nanotube network field-effect transistors*" Proc Natl Acad Sci USA 103, 921 (2006); and International Application WO2006-071,895, entitled "Nanoelectronic sensor devices for DNA detection and recognition of polynucleotide sequences", each of which is incorporated by reference.

Electrochemical schemes have been used for biomolecule detection. Electrochemical DNA and protein sensors which are based on conductors such as gold, carbon paste etc. are described, for example, in T G Drummond, M G Hill, and J K Barton, "*Electrochemical DNA sensors*" Nature Biotechnology 21, 1192 (2003); and in E Katz and I Willner, "*Probing biomolecular interactions at conductive and semiconductive surfaces by impedance spectroscopy: Routes to impedimetric immunosensors, DNA-Sensors, and enzyme biosensors*" Electroanalysis 15, 913 (2003), each of which is incorporated by reference.

SUMMARY OF THE INVENTION

Alternative embodiments of sensor devices and methods having aspects of the invention employ nanostructured electrode elements for detection of biomolecules, so as to advantageously enhance sensitivity by means measurement of electrochemical, impedance and related properties.

Embodiments having aspects of the invention may be suited for detection and measurement of biomolecular species such as polynucleotides, proteins, polysaccharides and the like.

Exemplary embodiments of detection or sensor devices having aspects of the invention employ nanostructured species as electrode material. A number of alternative species may be employed, such as nanotubes, nanoparticles, nanowires, nanocones and the like, alone or in combination. Similarly, graphene elements, such as monolayer sheets, may be included. A preferred species is a carbon nanotube (CNT) and more preferably a single walled carbon nanotube (SWNT). In the embodiments described in detail, SWNTs are disposed in randomly oriented interconnecting networks deposited or formed adjacent a substrate surface.

Preferably the sensors are adapted for operation in media such as biological buffers. Redox couple species may be included in detection media (e.g., ferrocyanide/ferricyanide redox couple) to enhance electron transfer between the media and the nanostructured electrode material, such as SWNTs.

Exemplary embodiments include recognition biomolecules bound to or adjacent a sensor electrode region, such as biomolecules attached to carbon nanotubes of a random network. Blocking or inhibition layers or materials may be included in embodiments, for example so as to prevent non-specific binding of species present in a sample.

For example, in embodiments direct to detection and measurement of DNA, the recognition biomolecules may be ssDNA oligonucleotide capture probes. In other embodiments directed to protein detection and measurement, the recognition biomolecules may be an antigen or antibody with analyte specific activity. For example, in a method or device assessing a metabolic protein, a analyte-specific antibody may be employed for recognition. In an alternative example, in a diagnostic method assessing serum antibody status, an antigen specific to the analyte antibody may be employed for recognition.

Exemplary sensor device embodiments having aspects of the invention may include other electrodes in addition to a nanostructured recognition electrode (having a capture or recognition species). For example, a gate electrode, a reference electrode, a counter electrode, or the like may be included. Electrodes may be connected to suitable measurement circuitry and instruments conventionally used for signal measurement, recordation, display, power supply, signal processing logic operations, or the like. Detection may include measurement and comparisons of a variety of different electrical properties, including amphometric, transconductance and capacitance measurements; impedance spectroscopy; cyclic voltammetry; square wave voltammetry; or the like.

Exemplary sensor device embodiments having aspects of the invention may include, for example, a redox couple or reporter enzyme/substrate combination described in detail below with respect to DNA detection and is also useful when applied to protein species detection using the exemplary devices having aspects of the invention, and vice versa.

It should be understood that elements and methods described herein with respect to detection and measurement of a particular example of biomolecular analyte are also useful for other kinds of biomolecule analytes. For example a redox couple or reporter enxyme/substrate combination described in detail below with respect to DNA detection is also useful when applied to protein species detection using the exemplary devices having aspects of the invention, and vice versa.

An exemplary method embodiment for biomolecule detection and measurement having aspects of the invention, and employing a sensor device as described above (e.g., including a CNT electrode material), comprises the following steps:
1. A sensor device is provided with one or more capture molecules or species (e.g., by immobilization on nanotubes) that can specifically bind a target analyte biomolecule of interest (examples of capture species include synthetic and/or natural species such as oligomers, antibodies, antigens, cell surface receptors, and the like).
2. The sensor device is exposed to a sample that contains (or is suspected of containing) the target analyte of interest under conditions sufficient to promote binding of capture species to the target, so as to form one or more capture-target hybrids.
3. The sensor device is exposed to an environment that contains an enzyme-labeled molecule or species that has activity to bind to capture-target hybrid to form a capture-target-enzyme complex, but which does not substantially bind to the sensor in the absence of target analyte.
4. One or more rinsing or washing steps may be performed, e.g., to remove unbound enzyme-labeled molecules, unbound sample constituents, and the like. Alternatively, a fluidic circuit may be provided having one or more sensors connected in the circuit such that the sensor is sequentially contacted by fluids of different composition (e.g., sample fluid, redox buffer, "rinse" buffer, enzyme-label buffer) at appropriate times.
5. Optionally, suitable reference measurements may be made for comparison at selected points in the process. Alternatively, sensor signals may be measured or recorded on a continuous or real-time basis. Values may be sampled at selected sequence times or during selected periods for detection analysis.
6. Optionally, the sensor device is exposed to one or more redox couples to enhance detection signals.
7. The sensor device may be exposed to a solution containing a reporter substrate active with the enzyme. Enzyme and substrate are selected in such way that the product of enzyme activity has the property of interacting with nanotubes, for example by means of physical adsorption, so as to produce a detectible change in sensor electrical properties. For example, an enzyme/substrate product which is adsorbed onto nanotubes may alter nanotube electrochemical properties in one or more of the following ways:
    a. The product changes the electrochemical activity by impeding or enhancing electron tunneling from nanotubes to electrolyte.
    b. The product is electrochemically active by itself so as to contribute to a measurable electrochemical signal.
8. One or more electrical measurements are performed, and analyzed to determine analyte presence and/or concentration.

Note both steps 2 and 3 include exposing the target analyte to a molecule or species having specificity for binding the target analyte. Note that the same or similar binding molecules or species may be employed in each of these steps, or they may be different and may have different degrees of binding affinity. For example step 2 may employ a monoclonal antibody as a capture species, and step 3 may employ a polyclonal antibody as an enzyme-labeled species. The overall effect of the target-binding specificities of the capture species and the enzyme-labeled species provides that the capture-target-enzyme complex will only be formed in step 3 in response to the presence of the target analyte.

Note that a variety of different buffer compositions known in the art may be employed in the methods herein (AP buffer, PBS buffer and the like). Typically, the buffer approximates physiologic salinity and promotes an approximately neutral pH with a suitable buffering couple. Preferably, a buffer composition is selected or modified to suit the biochemistry being employed at a particular step. Different buffer compositions may be employed at different steps, as required.

For example, for oligomer capture and binding species, buffers (and optionally stringency factors) may be selected to promote hybridization of complementary polynucleotide strands while minimizing nonspecific binding. In another example, buffers may be selected to promote specific antibody-antigen binding. In yet another example, buffer composition (which may include cofactors) may be selected to promote the activity of a label enzyme on a reporter substrate. A non-phosphate buffer, such as a tris-based buffer, may be used with an alkaline phosphatase enzyme/reporter system to avoid inhibition of the alkaline phosphatase by organic phosphate.

Alternative Electrical Properties. Embodiments having aspects of the invention may detect an analyte via measurements made via a working electrode and a counter or reference electrode (also called a gate), which measure either (a) Faradaic electrochemical effects (where there is charge transfer between an solution and the working electrode, such as amperiometric methods), or (b) non-Faradaic effects (where there is alteration of capacitance or impedance properties). Likewise, embodiments may measure a combination of these, a sequential measurement of both of these. See description below with respect to FIG. 14 in this regard.

Reporter Catalysts. In the examples described in detail herein and shown in the Figures, a reporter catalyst complex comprises an enzyme conjugated or complexed with a capture species active to bind to an analyte species.

However, in alternative embodiments having aspects of the invention, the reporter catalyst may be one of a number of materials or compounds, such as a catalytic metal nanoparticle, conjugated to a capture species. A suitable reactant may be applied in the manner described herein with respect to enzyme-active substrates, so as to create a catalytic product producing a detectable change in electrochemical response of the device (e.g., device 20 shown in FIGS. 4 and 8). The product may be a soluble species (e.g., producing electroactive enhancement), or may be an insoluble species (e.g., depositing on network 14 so as to produce current suppression).

Alternative Reporters. In further embodiments having aspects of the invention, a reporter complex may include an electroactive species directly producing a detectable signal (e.g., electrochemical charge transfer or non-faradic impedance or capacitance).

In still further alternatives having aspects of the invention, where an analyte is a polynucleotide and the capture species includes a complementary nucleotide sequence, a reporter species may include an electro-active intercalator having a binding or insertion activity specific to duplex form of polynucleotides so as to be immobilized upon exposure to hybridized analyte-capture species. The electro-active intercalator may provide a detectable signal, such as by inducing charge transfer in an electrochemical reaction, or may have polarity effects modifying impedance or capacitance.

For further description of non-enzyme catalysts, electroactive groups and intercalators (among other things), see E. Palecek, F. Scheller and J. Wang, Ed., "*Electrochemistry of Nucleic Acids and Proteins*"; Perspectives in Bioanalysis, Vol. 1; Elsevier, Amsterdam, 2005, which publication is incorporated by reference.

It should be noted that while embodiments employing the forgoing principles may include working electrodes comprising conventional conductive materials, the employment of nanostructured materials (such as carbon nanotubes, and preferably an interconnecting network of carbon nanotubes), produces better performance, higher signal-to-noise, and also provides effective binding base for both capture species. See discussion below with respect to FIG. 12 in this regard. In addition, carbon nanotubes, in current suppression embodiments, provide effective deposition base for electro-suppressive reporter products, so as to produce enhanced detection signal characteristics.

In certain embodiments having aspects of the invention, detection system comprises a sensor having a working electrode, preferably including a carbon nanotubes (CNT), such as a network of CNTs. The sensor may also include a counter electrode, which may be a reference electrode. The electrodes are configured to communication with measurement circuitry (which may be separate, such as where the sensor is disposable). A first capture species having analyte binding affinity may be bound to a sensor surface on or adjacent the working electrode, and preferably comprises a first capture specie bound to CNTs defining an electrode surface (alternative capture species dispositions are possible, e.g. using microfluidic communication with the electrodes). Examples of capture species include antibodies, antigens and oligonucleotides.

In method embodiments having aspects of the invention a sensor such as described above is provided. In any operative order or simultaneously, (a) a sample possibly containing analyte is exposed to the sensor so as to bind analyte species to the first capture species; and (b) a reporter complex including a second capture species having analyte binding affinity is exposed to the sample and/or the sensor so that reporter complex is bound to the analyte. Following steps (a) and (b), in the event analyte is present in the sample, an immobilized analyte-reporter group is formed including capture species 1, analyte and reporter complex. Subsequently, the sensor may be washed to remove unbound reagent and sample.

In certain embodiments, the immobilized analyte-reporter group has properties which produce a detectable electrical effect (e.g., charge transfer to electrodes or polarity effects on capacitance) which may be measured to determine analyte presence in the sample. For example, the reporter complex by include an electroactive species influencing electrode charge transfer (e.g., ferrocene) or a species inducing charge polarity so as to influence capacitance measure via an electrode. Where an analyte is a polynucleotide and the first capture species includes a complementary nucleotide sequence, the reporter complex may include an electro-active intercalator.

In further embodiments, the reporter complex includes a catalyst having an activity for a selected reporter substrate to produce a product species, the product species configured to interact with the working electrode so as to produce a detectable change in an electrical property (e.g., charge transfer in an electrochemical reaction or electrolytic capacitance). The immobilized analyte-reporter group may be exposed to the reporter substrate so as to product the product, resulting in the detectable property change, so as to indicate the presence or concentration of the analyte in the sample. In certain embodiments, the catalyst may include an enzyme having activity for reporter substrate to produce the product.

Where the catalyst and substrate are selected so that the product has a property which induces a change in electron transfer at the working electrode, the product property may be the production of electrochemical charge transfer, or alternatively (or additionally) the product may inhibit charge transfer in an electrochemical reaction with the electrode environment.

In further description, the embodiments having aspects of the invention are illustrated by examples in which the reporter catalyst complex comprises an enzyme which is active to produce a product upon exposure, under suitable conditions, to a reporter substrate.

The claims set forth below provide further description of inventive devices and methods, constitute a portion of the specification of this application, and should be read and understood as part of this Summary of the Invention as if set forth herein in full.

SUMMARY OF FIGURES

The figures may be briefly summarized as follows:

FIG. 1 shows architecture of a sensor device embodiment having aspects of the invention for detection and measurement of biomolecular species such as polynucleotides, proteins, polysaccharides and the like.

FIGS. 13A and 13B show two views of an alternative sensor embodiment functionally similar to that shown in FIG. 8, having an alternative geometric arrangement.

FIG. 13C show an alternative embodiment of a reporter enzyme complex having multiple linked enzyme species.

FIG. 14 shows the equivalent circuit of the device of FIG. 1 shown by the Randles model, where faradic and capacitance processes are represented.

FIGS. 15A and 15B show longitudinal and cross-sectional views, respectively, of an alternative lumen-like sensor system embodiment 150 having aspects of the invention, FIGS. 16A and 16B show longitudinal and cross-sectional views, respectively, of an alternative conduit sensor system embodiment 160 having aspects of the invention.

FIG. 16C shows schematically one possible stacked array or matrix mounting of sensor systems having aspects of the invention.

FIGS. 17, 18A-18H, and 19 show exemplary embodiments of microprobe sensors configured as resistive or transconductance sensors.

FIGS. 20 and 21A-21F show exemplary embodiments microprobe sensors configured as electrochemical sensors.

FIGS. 29 and 29A-29C show differing views of an exemplary embodiment of a migration assay device having aspects of the invention. FIG. 29A is a cross-sectional view of the embodiment shown in FIG. 29 taken along the line A-A. FIG. 29B is a cross-sectional view of the embodiment shown in FIG. 29 taken along the line B-B. FIG. 29C shows an exploded detail of the sensor platform of the embodiment shown in FIG. 29.

FIG. 29D shows an alternative configuration of a sensor platform, with respect to the device shown in FIG. 29.

FIGS. 30, 30A, and 30B shows differing views of an alternative single-port embodiment of a migration assay having aspects of the invention. FIG. 30A is a cross-sectional view of the embodiment shown in FIG. 30 taken along the line A-A. FIG. 30A is a cross-sectional view of the embodiment shown in FIG. 30 taken along the line B-B.

DESCRIPTION OF THE INVENTION AND EXAMPLES

Exemplary Sensor Devices

Figure 1:
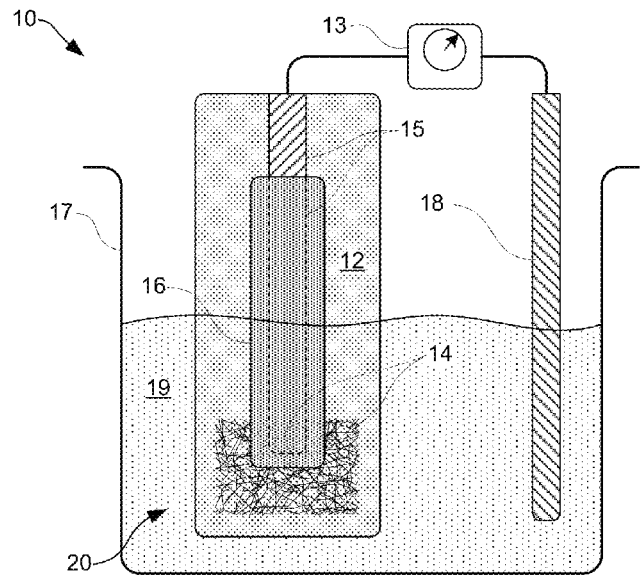

FIG. 1 shows schematic architecture of a sensor device embodiment having aspects of the invention for detection and measurement of biomolecular species such as polynucleotides, proteins, polysaccharides and the like. In a particular example, device 10 may be employed for DNA detection. The device 10 comprises a sensor substrate 12 (e.g., comprising PET, polycarbonate, flexible polymers, or the like) having a reaction or sensor tip portion of its surface 20 on which an interconnecting carbon nanotube (CNT) network 14 is disposed.

In the example of FIG. 1, a conductive trace or drain 15 electrically communicates with the network 14 (e.g., silver ink may be deposited on the substrate 12 so as to contact a portion of the network 14).

Device 10 includes a well or container 17 holding buffer or fluid media 19 in which both sensor tip 20 and a gate electrode 18 are immersed. In certain embodiments, gate electrode 18 may include a reference electrode, such as a Ag/AgCl reference electrode, saturated calomel electrode, or the like. One skilled in the art will appreciate that container 17 may comprise one or more microfluidic elements, capillaries, sampling devices, incubators, and the like, without departing from the spirit of the invention.

An encapsulation material 16 (e.g., polymers such as epoxy, $Al_2O_3$, $Si_4N_3$, $SiO_2$, ALD layers, and the like) may be deposited so as to isolate portions of the device from the medium or buffer 19, while not covering at least a portion of the CNT network 14.

With reference to encapsulation material 16 and to other encapsulation layers, dielectric layers and/or isolation layers or multi-layer structures included in alternative embodiments having aspects of the invention described herein, it may be advantageous to produce layers that are extremely thin and uniform, while at the same time avoiding pores, shadowing or other discontinuities/irregularities in the coating. It may also be desirable in certain elements to avoid damage to underlying elements, such as carbon nanotube networks. Atomic layer deposition methods provide alternative approaches to producing a layer or coating having these desirable qualities, and may be employed to deposit a layer of an oxide, nitride or other compound, or combinations or multiple layers of these. Alternative methods may be used, such as thermal and e-beam evaporation. Additional process elements may be included to improve coating properties, such as rotating and/or tilting a substrate during evaporation. Further description of ALD methods may by found in P. Chen, et al, "Atomic Layer Deposition to Fine-Tune the Surface Properties and Diameters of Fabricated Nanopores", Nano Lett (June 2004) Vol. 4, No. 7, pp 1333-37; D. Farmer et al, "Atomic Layer Deposition on Suspended Single-Walled Carbon Nanotubes via Gas-Phase Noncovalent Functionalization", Nano Lett (March 2006) Vol. 6, No. 4, pp 699-703; and M. Groner et al, "Gas diffusion barriers on polymers using Al2O3 atomic layer deposition", Appl. Phys. Lett. (2006) Vol. 88, pp 051907-1; which publications are incorporated by reference.

Drain 15 and gate 18 are connected to suitable measurement circuitry 13, which may comprise one or more of a number of devices conventionally used for signal measurement, recordation, display, power supply, signal processing and/or logic operations, and the like, as described further herein. Additional or substitute electrodes may also be included in device 10, such as counter electrodes, reference electrodes and the like, such as Ag/AgCl reference electrodes described herein.

A CNT network may be made directly on a device substrate (e.g. by CVD formation of CNT from catalyst nanoparticles, see US 2007-0140946 which is incorporated by reference). In certain embodiments, the CNT network may be initially deposited on a deposition membrane, such as by suction or solvent absorption deposition on a filter membrane (e.g., alumina or polycarbonate nanoporous filters are commercially available). The deposition membrane may be affixed to a device substrate as a substrate surface layer, or the CNT network may be transferred from the deposition membrane to a device substrate, such as a flexible polymer (e.g., by "floating" in a fluid). In some embodiments, the device substrate itself may comprise a porous material permitting suction or solvent absorption deposition.

In certain embodiments, a CNT network may be deposited on a device substrate by spray deposition and the like. For example, SWNTs and/or other nanoparticles may be suspended in a suitable fluid solvent, and sprayed, printed or otherwise deposited in a substrate. The SWNTs or other nanoparticles may optionally have additional functionalization groups, purification and/or other pre-deposition processing. For example SWNTs functionalized with poly m-aminobenzene sulfonic acid (PABS) show hydrophilic properties and may be dispersed in aqueous solutions.

One or more conductive traces or electrodes may be deposited after deposition, or alternatively, the substrate may include pre-patterned electrodes or traces exposed on the substrate surface. Similarly, alternative embodiments may have a gate electrode and a source electrode supported on a single substrate. The substrate may include a flat, sheet-like portion, although one skilled in the art will appreciate that geometric variations of substrate configurations (rods, tubes or the like) may be employed without departing from the spirit of the inventions.

Multiple light, uniform spray steps may be performed, e.g., with drying and resistance testing between spray steps, until the network sheet resistance reaches a target value (implying a target network density and conductivity). In one example, P2-SWNTs produced by Carbon Solutions, Inc of Riverside, Calif. were spray-deposited on a portion of a PET sheet substrate with pre-patterned traces until a sheet resistance about 1 k$\Omega$ was reached.

See also the methods for making nanotube networks as well as additional device and substrate alternatives as described the following patent applications, each of which is incorporated by reference: US Application 2007-0140946 entitled "Dispersed Growth Of Nanotubes On A Substrate"; US Application 2005-0184641 entitled "Flexible nanotube transistors"; US Application 2007-0208243) entitled "Nanoelectronic Glucose Sensors"; and U.S. application Ser. No. 11/636,360 filed Dec. 8, 2006 (now U.S. Pat. No. 8,152,991), entitled "Ammonia Nanosensors, And Environmental Control System".

Redox Couple Species to Enhance Electron Transfer.

Figure 2:
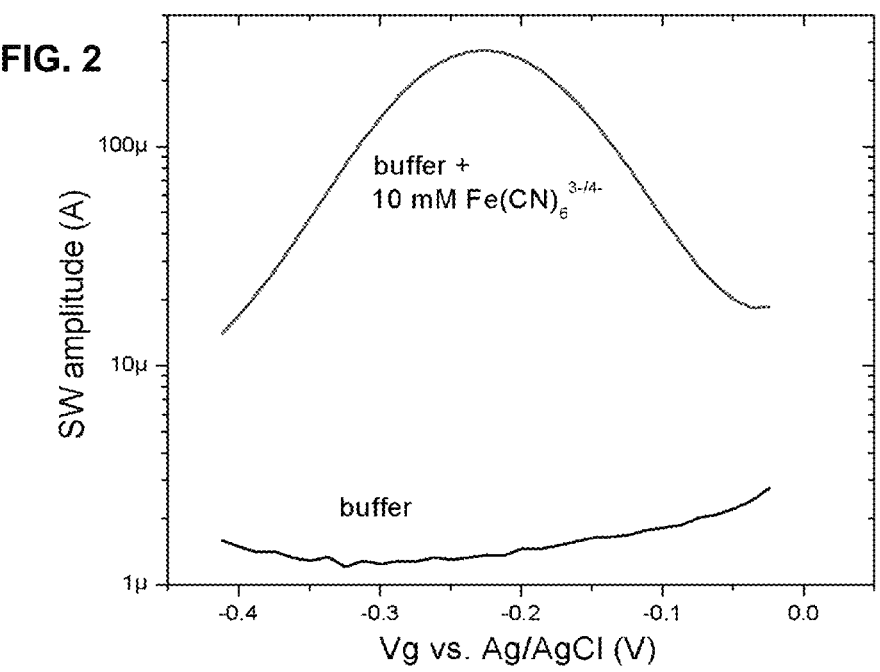
FIG. 2 shows an example of square wave voltammetry (SWV) response of a nanotube electrode such as shown in FIG. 1, illustrating the effect of a ferrocyanide/ferricyanide redox couple.

FIG. 2 shows an example of square wave voltammetry (SWV) response of a nanotube electrode such as shown in FIG. 1 in buffer alone (lower curve), as compared with the response in a buffer with added redox couple (upper curve). In this example, the redox couple includes 10 mM solution of $Fe(CN)_6^{3-/4-}$ added to AP buffer. As it can be seen from FIG. 2, the ferrocyanide/ferricyanide redox couple produces more than 100 fold increase of electron transfer between solution and the device as indicated by square voltammetry method. The device shows purely electrochemically capacitive behavior in buffer alone, but converts to "resistor" in the presence of ferrocyanide/ferricyanide redox couple. Square voltammetry methods are further described in A J Bard and L Faulkner, *Electrochemical Methods: Fundamentals and Applications* (Wiley and Sons, New York, 2001); and J Wang, Analytical Electrochemistry (Wiley and Sons, New York, 2000), which publications are incorporated by reference.

Figure 3:
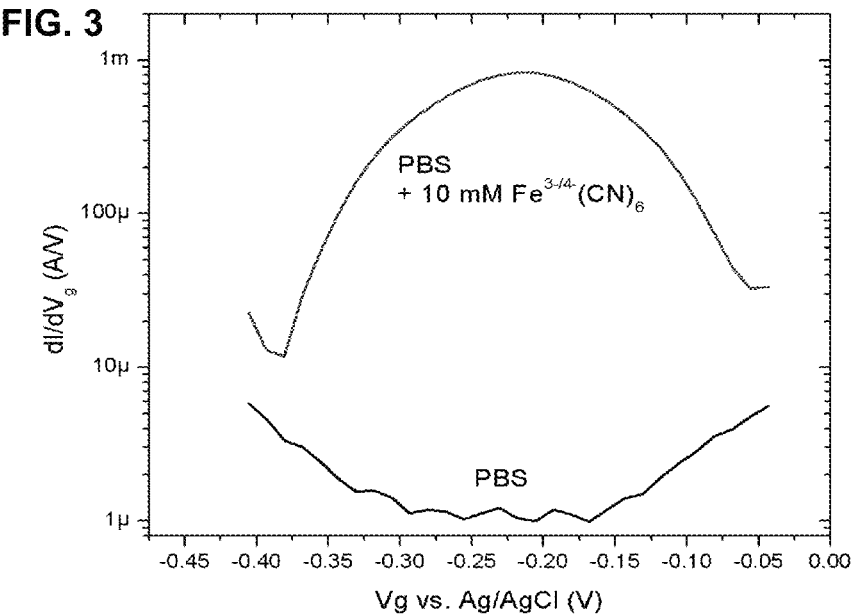
FIG. 3 shows an example of differentiating cyclic voltagrams (CV) illustrating the response of a nanotube electrode such as shown in FIG. 1 with a ferrocyanide/ferricyanide redox couple.

As shown in FIG. 3, further amplification of the dynamic range can be achieved by differentiating cyclic voltagrams (CV): The maximum of the derivative of the totally reversible system is close to the half-potential value, which happens to be around −230 mV versus Ag/AgC reference electrode. With this approach the response is extended to three orders of magnitude, comparing the response with buffer alone (lower curve) versus buffer with ferrocyanide/ferricyanide redox couple (upper curve).

In addition or in substitution to the ferrocyanide/ferricyanide redox couple described, alternative redox couple species may be employed without departing from the spirit of the invention.

EXAMPLE 1

DNA Detection

Suppression of Redox Couple Electron Transfer by Target/Catalyst/Substrate Reaction In certain embodiments having aspects of the invention, an analyte biomolecule may be detected by measurable changes in the electron transfer between the redox couple and the nanotube electrode 14 of the device 10, mediated by an target-bound catalyst/substrate reaction (in this example, comprising an enzyme as a catalytic group).

Figure 4:
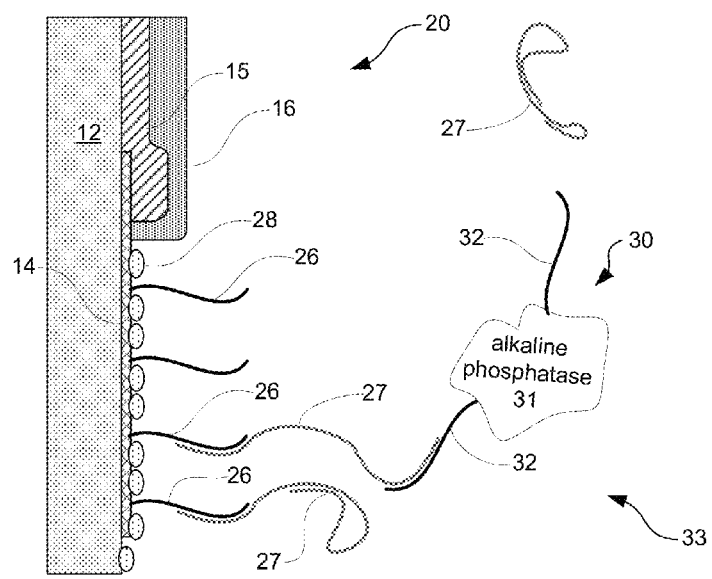
FIG. 4 shows an exemplary embodiment of the sensor tip portion of a sensor device such as is shown in FIG. 1, in which the nanotube network is functionalized by ssDNA capture probes, forming a capture/target/enzyme complex

FIG. 4 shows one exemplary embodiment of the sensor tip portion 20 of a sensor device such as is shown in FIG. 1, in which the nanotube network 14 is functionalized by ssDNA capture probes 26 having at least one sequence complementary to a corresponding selected sequence of target analyte polynucleotide 27, the probes 26 being immobilized or bound adjacent the nanotube network 14; the surface 12 of the sensor or both. Probes 26 may be made using conventional methods of making oligonucleotides such as probes and primers having a selected base sequence. Reference measurements may be made in a buffer with redox couple (e.g., ferrocyanide/ferricyanide) of tip 20 having capture probes 26 immobilized, and the reference signals may be recorded.

See also the various alternative means of immobilizing oligonucleotide probes on nanoparticles such as SWNTs or substrates (among other things) as describe in International Application WO2006-071,895 entitled "Nanoelectronic sensor devices for DNA detection and recognition of polynucleotide sequences", which is incorporated by reference.

Target analyte 27 may be hybridized and bound to probe 26 upon incubation under suitable conditions. One skilled in the art will appreciate that probe-target sequence selection, buffer composition, stringency factors and combinations of these may be adjusted and used so as to promote hybridization of probes to selected target sequences without undue non-complementary binding, non-analyte binding, dysfunctional probe or target configurations, or the like. Optionally additional materials and functionalization 28 may be deposited adjacent the sensor tip region 20 to inhibit nonspecific binding.

Figure 5:
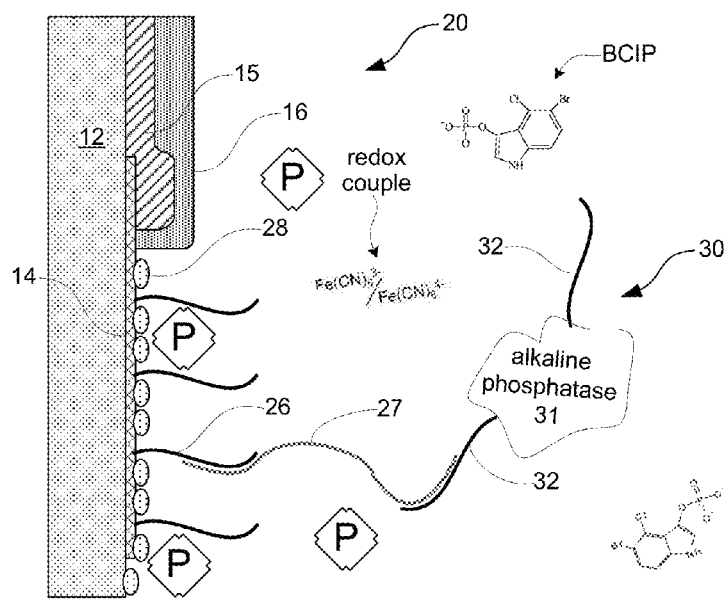
FIG. 5 shows the embodiment of FIG. 4, further exposed to BICP substrate.

As shown in FIGS. 4 and 5, reporter enzyme complex 30 comprises alkaline phosphatase 31 to which one or more label probes 32 are bound. Like probes 26, probes 32 have at least one sequence complementary to a corresponding selected sequence of target analyte polynucleotide 27. For example, one or more biotinylated probes 32 may be bound to alkaline phosphatase 31 conjugated with streptavidin to form an enzyme complex 30.

As schematically shown in FIG. 5, in one method embodiment, tip 20 of sensor 10 is incubated in a buffer including both a sample being tested for target analyte 27 and a quantity of enzyme complex 30, under conditions suitable to induce hybridization of target analyte 27 to both sensor probes 26 and enzyme complex probes 32, to as to form a bound target/enzyme/sensor complex 33. The tip 20 may be rinsed following incubation to remove any unbound polynucleotides and enzyme complex. In embodiments including fluidic circuitry, unbound polynucleotides and enzyme complex may be removed by continued flow of buffer.

As shown in FIG. 5, the sensor tip 20 with target/enzyme complex 27, 30 is incubated in a buffer comprising BCIP substrate (bromochloroindolyl phosphate, $C_8H_6NO_4BrClP \cdot C_7H_9N$). The alkaline phosphatase 31 converts BCIP to an insoluble product "P" that precipitates on the region of sensor tip 20 and particularly on or adjacent to nanotube electrode 14 (for example, by hydrolysis of the phosphate groups of the BCIP and creation of an insoluble dimer). The precipitated product P inhibits electrochemical current between nanotubes and the ferrocyanide/ferricyanide redox couple. Detection measurements in buffer with the redox couple may be made, and comparison with reference signals may be made to quantify the effect of analyte-triggered blocking of the electrochemical current.

Figure 6:
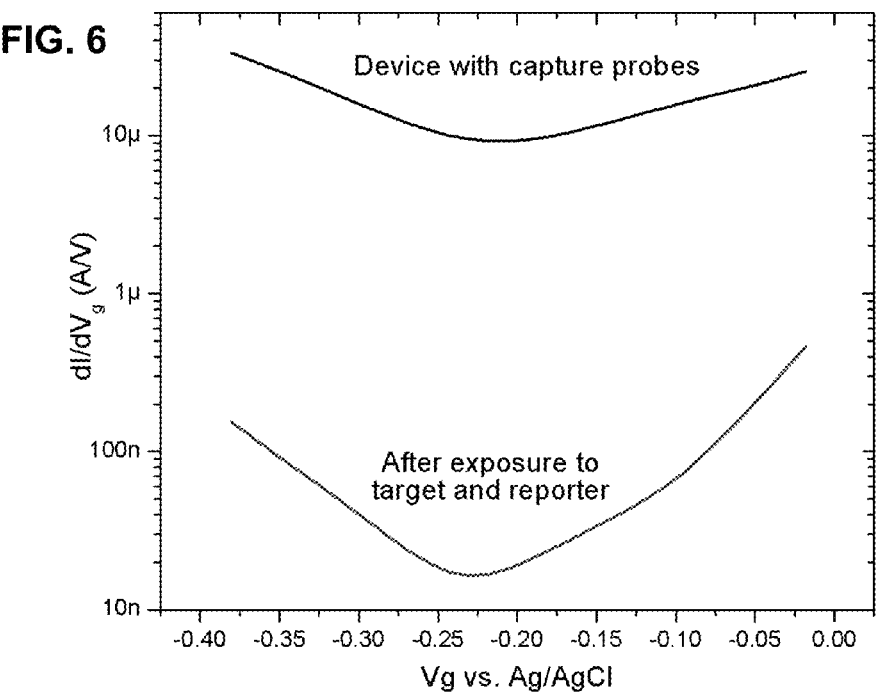
FIG. 6 shows a response of a device such as shown in FIGS. 4-5, both before and after exposure to label enzyme and reporter substrate.
Figure 7:
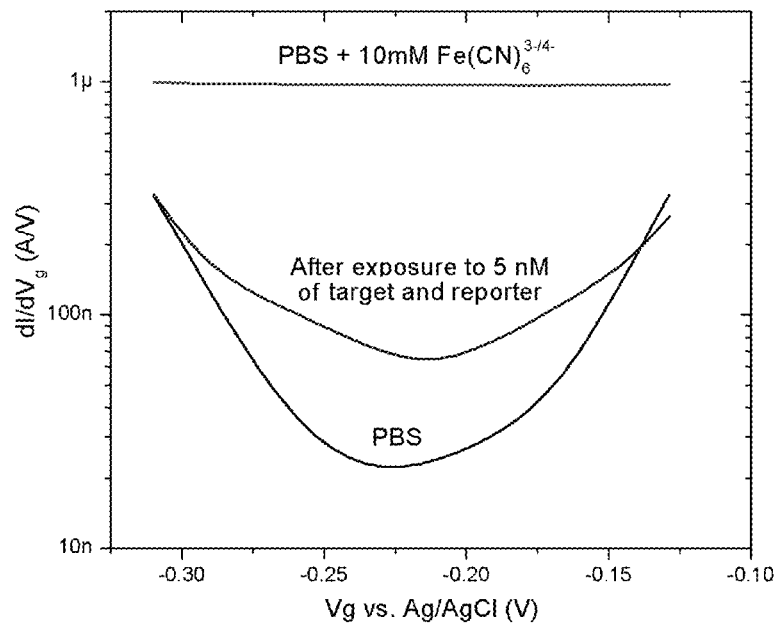
FIG. 7 shows a the response of a device such as shown in FIGS. 4-5, with a more dilute target sample.

FIGS. 6 and 7 illustrate the effect of an exemplary target/enzyme complex reacting with a reporter substrate so as to suppress the redox couple electron transfer, as measured by resultant signals from a sensor device such as illustrated in FIGS. 1 and 4.

With respect to FIG. 6, the device was first incubated with ssDNA capture probes, and the reference measurement was taken in buffer solution with ferrocyanide/ferricyanide redox couple (upper curve). Subsequently, the device was incubated with biotinylated target ssDNA strand at 5 μM concentration for 30 minutes. Next alkaline phosphatase conjugated with streptavidin was added as a reporter (10 minute incubation). Finally, the device was exposed to BCIP substrate (30 minute incubation). Measurements were then repeated to obtain a detection signal (lower curve). Comparison of reference and detection measurements indicate that the redox current was suppressed by three orders of magnitude, so as to, in effect, convert the electrochemical "resistor" back to "capacitor".

With respect to FIG. 7, the device and method of FIG. 6 were repeated, using a much more dilute target sample comprising biotinylated target sequence at 5 nM concentration. The device was functionalized with ssDNA capture probes, and the reference measurement was taken in buffer alone (bottom curve). A second reference signal was measured during exposure to ferrocyanide/ferricyanide redox couple (upper curve). The device was then incubated with biotinylated target ssDNA strand at 5 nM concentration, followed by exposure to streptavidin-conjugated alkaline phosphatase, followed by exposure to BCIP substrate, in the manner described with respect to FIG. 6. A detection signal was then measured (middle curve). It may be seen by comparison of the curves in to FIG. 7 that the target-triggered BCIP product precipitation led to the decrease of the electrochemical signal by over one order of magnitude by suppression of the redox current. Note that the middle detection curve is similar in shape but still somewhat above the level of the first non-redox reference curve.

Blocking or inhibition layers or materials may be deposited or applied to the sensor tip 20 and nanotube electrode 14 so as to prevent non-specific binding of species present in a sample or reaction buffers, such as excess alkaline phosphatase and the like.

In one embodiment, enzyme complex 30 may be made as a pre-prepared reagent. In an alternative embodiment, probes 32 and alkaline phosphatase 31 are self-assembled during sensor operation by addition of precursors to the medium (e.g., biotinylated probes 32 and streptavidin-conjugated alkaline phosphatase 31) to make enzyme complex 30 in situ.

In one embodiment, Sensor device 10 may be supplied as a kit having a plurality of alternative probes 26 and probes 32, such as for the detection of different target analytes. In another embodiment, an array or matrix comprising a plurality of devices 10 may be provided, and may be configured to detect a plurality of different analytes.

In an alternative method embodiment, a sample may be purified and/or pre-processed (e.g., purified by magnetic bead and selective probes methods) so that any target analyte present is labeled or conjugated with alkaline phosphatase 31 (e.g., biotinylation of purified analyte and reaction with streptavidin-conjugated reporter enzyme) so as to be capable of producing a target/enzyme/sensor complex without the use of enzyme complex probes 32.

In addition or in substitution to the alkaline phosphatase/BCIP reporter reaction described, alternative enzyme-reporter substrate systems may be employed without departing from the spirit of the invention.

One alternative method embodiment for DNA detection and measurement having aspects of the invention comprises the following steps:

a. The ssDNA capture probes 26 having sequences complementary to a target analyte polynucleotide 27 are immobilized on nanotube network 14; on the surface 12 of the sensor or both.

b. The sensor with ssDNA capture probes exposed to a suitable reference media (e.g., a biological buffer such as PBS) with added redox couple (e.g., 10 mM ferrocyanide/ferricyanide).

c. One or more selected parameters of the nanotube-redox couple interactions may be recorded (e.g., square wave, cyclic, and impedance voltammetry) as one or more reference signals, measured and/or recorded by suitable circuitry (13 in FIG. 1) connected to at least the drain 15 and gate 18 electrodes.

d. The sensor is incubated in a hybridization buffer which includes (1) a sample being tested for target DNA 27, and (2) also includes a quantity of reporter complex comprising DNA strand probes attached to a alkaline phosphatase enzyme (see FIGS. 4 and 5). Note, step d. may be done in combination or as two separate substeps. Following incubation the sensor is rinsed in additional buffer to remove unhybridized reporter complex and sample material e. The sensor is exposed to a buffer including BCIP substrate, and permitted to react. If target analyte 27 is present in the sample, BCIP substrate is converted by action of alkaline phosphatase to an insoluble product "P" that precipitates so as to form a coating or deposit on the on nanotube network 14; on the surface 12 of the sensor or both.

f. The insoluble reaction product P produces detectable changes in sensor properties, for example by acting as a blocking agent for the redox current to the sensor, in which the precipitate inhibits electrochemical current between nanotubes 14 and redox couple. One or more detection signals may be measured, for example in the manner in which the reference signals are measured in Step c above. For example, the detection signals may be measured with the sensor in the enzyme reaction buffer, or alternatively the sensor exposed to a reference buffer.

g. The one or more detection signals are compared with the one or more reference signals and differences in signals are analyzed to determine target analyte presence and/or concentration in the sample. For example, a decrease of the redox current parameters may be correlated to a target DNA concentration.

EXAMPLE 2

Protein Detection by Faradic Current Suppression

As described above, protein detection may be performed using a sensor device 10 such as shown in FIG. 1. A capture species having activity specific to a protein target analyte may be immobilized on or adjacent the nanostructured electrode material (e.g., nanotube network 14) on substrate tip region 20. In one example, a sensor device 10 is functionalized for streptavidin detection as an analyte.

Figure 8:
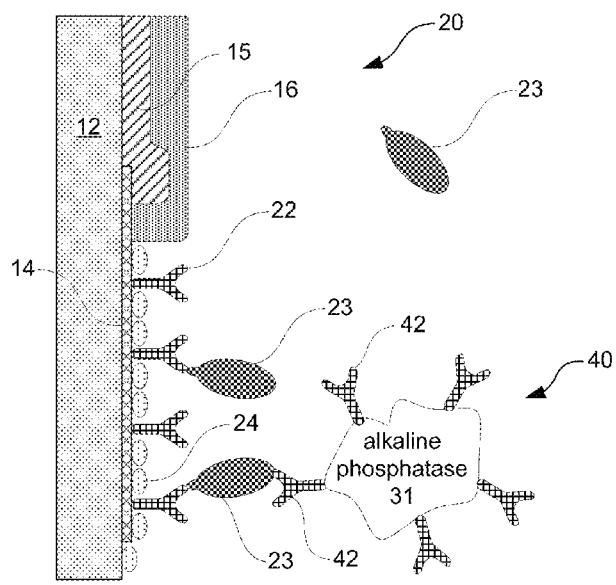
FIG. 8 shows one exemplary embodiment of the sensor device such as is shown in FIG. 1, in which the nanotube network is functionalized by an antibody capture species, for detection of a protein analyte.

FIG. 8, shows one exemplary embodiment of the sensor tip portion 20 of a sensor device such as is shown in FIG. 1, in which the nanotube network 14 is functionalized by capture species 22 (e.g. anti-streptavidin antibody) specific to analyte of interest 23 (e.g., streptavidin), the capture antibodies 22 being immobilized or bound adjacent the nanotube network 14; the surface 12 of the sensor or both.

In one example, anti-streptavidin antibodies are adsorbed onto nanotube walls by exposing tip 20 and nanotube network 14 to a solution comprising 10 μg/ml antibodies in phosphate-buffered saline (PBS) solution for 14 hours at 4 C degrees.

Reference measurements may be made in a buffer with redox couple (e.g., ferrocyanide/ferricyanide) of tip 20 having capture probes 22 immobilized, and the reference signals may be recorded.

A reporter catalyst complex 40 (in this example, comprising an enzyme as a catalytic group) comprises a reporter enzyme 31 (e.g., alkaline phosphatase) bound to one or more binding species 42 (e.g. anti-streptavidin antibody). As may be seen, an analyte species 23 may bind to both capture species 22 and binding species 42 so as to form an device/analyte/enzyme complex. For example, reporter enzyme complex 40 may comprise alkaline phosphatase labeled with a anti-streptavidin antibodies as binding species 42.

Figure 9:
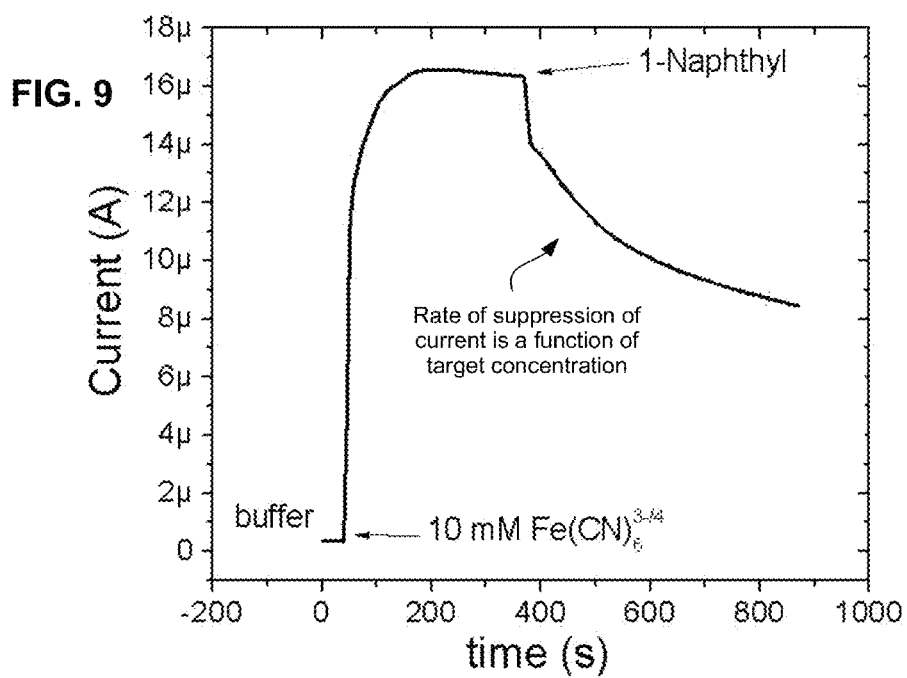
FIG. 9 is a plot illustrating the response of a device such as shown in FIG. 8 functionalized with anti-streptavidin capture species, detecting streptavidin labeled with enzyme alkaline phosphatase, upon exposure to 1-Naphthyl reporter substrate in the presence of a redox couple.
Figure 10:
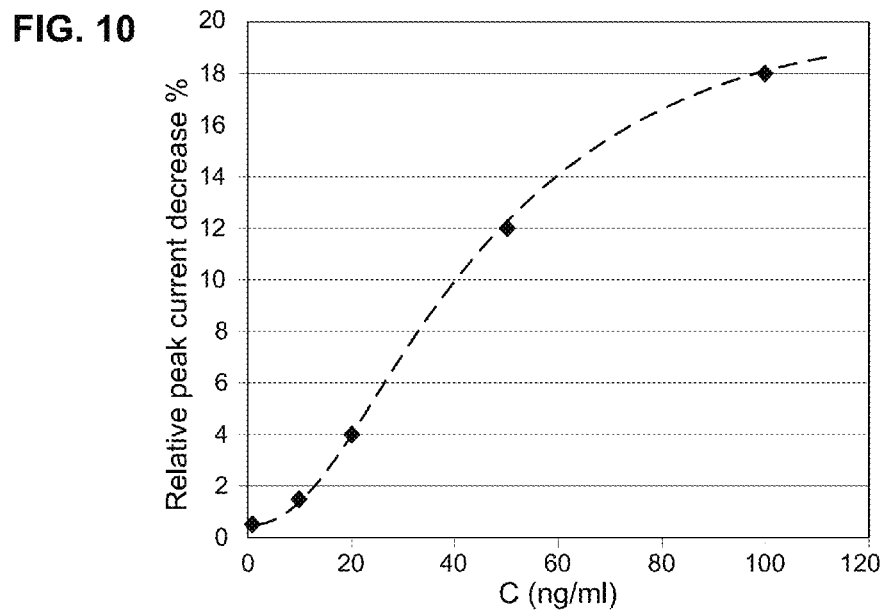
FIG. 10 shows the relationship between concentration and relative current decrease for a reaction such as is plotted in FIG. 9.

In the example represented by the data shown in FIGS. 9 and 10, an analyte/enzyme complex is employed to demonstrate the combination of steps 2 and 3 of the method example described in the "Summary of the Invention" above (e.g., combination of 23 and 40 in FIG. 8). Tip 20 may be immersed in a solution containing streptavidin labeled with enzyme alkaline phosphatase in PBS for 30 minutes at room temperature, after that the device is thoroughly washed with bare PBS and placed in 100 mM Tris 1 mM MgCl2 1 mM ZnCl2 pH 8 (APB) buffer. Electrical measurements may be performed (circuitry 13) at this point as a first reference signal.

Subsequently, tip 20 may be washed thoroughly with fresh PBS and placed in a solution comprising about 2% of 0.05% Tween 20 (polyoxyethylene sorbitan mono-laurate, a non-ionic surfactant); BSA (bovine serum albumin); and PBS solution for 2 hours at room temperature to introduce a BSA blocking layer (24 in FIG. 8).

As was noted with respect to Example 1 above for DNA detection, a redox couple may be added to the medium to enhance the electron transfer between solution and the device for protein and other biomolecule detection as well. For example, a ferrocyanide/ferricyanide redox couple may be added to the detection buffer (see FIGS. 2 and 3 and description above).

In this example, a reporter enzyme/substrate combination may be alkaline phosphatase acting on a 1-Naphthyl substrate. 1-Naphthyl is converted by alkaline phosphatase to 1-Naphthol (product) that is further oxidized in the electrochemical environment of the detection solution. See for example E Palecek, R Kizek, L Havran, S Billova, and M Fojta, "*Electrochemical enzyme-linked immunoassay in a DNA hybridization sensor*" Anal Chim Acta 469, 73 (2002), which publication is incorporated by reference.

Measurements such as square wave (SW) current may be used to monitor the detection reactions. In the example shown in FIG. 9, the device was incubated with 20 ng/ml streptavidin-alkaline phosphatase (SAv-AP) conjugate for 30 minutes in PBS. A gate voltage Vg (versus an Ag/AgCl reference electrode) of about −250 mV was applied. As shown in FIG. 9, the current increased dramatically upon addition of the ferrocyanide/ferricyanide redox to a maximum value. Upon addition of 2 mM of 1-Naphthyl substrate to the detection buffer, the current is rapidly suppressed as enzyme activity produces Naphthol. For a broad range of analyte/enzyme complex concentrations (concentration in sample, and consequently amount hybridized to device capture species), this suppression follows an exponential relationship with time. The rate of current suppression then becomes a function of analyte concentration. As shown in FIG. 9, a time domain may be selected to determine the rate of current suppression (in this case a segment of 200 s).

FIG. 10 shows that a consistent relationship between concentration and relative current decrease may be obtained. The data is plotted for a range of streptavidin concentration over two orders of magnitude (about 1 to about 100 ng/ml).

EXAMPLE 3

Protein Detection by Electrochemically Active Reporter

Figure 11:
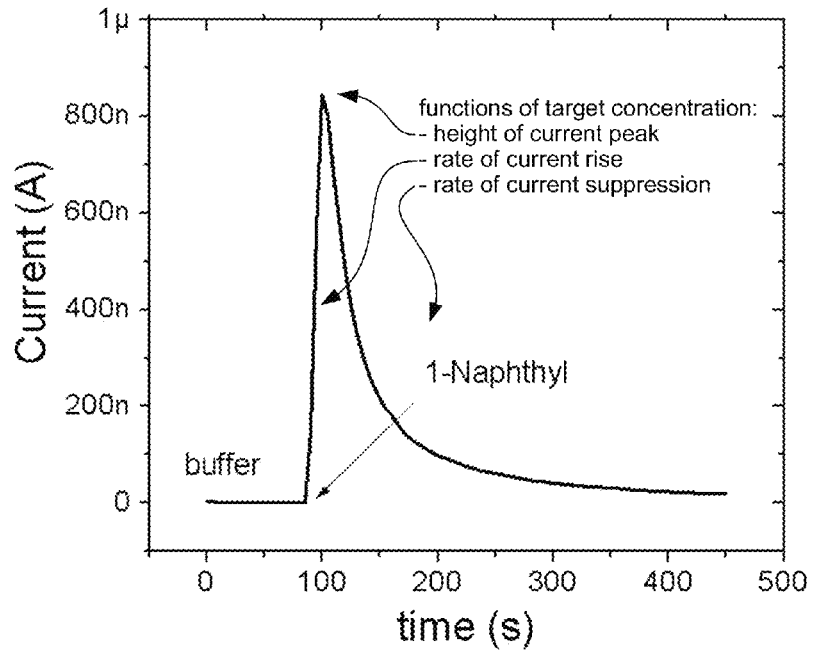
FIG. 11 shows the effect of 1-Naphthyl as a reporter substrate, illustrating the effect of the enzyme product 1-Naphthol as an electrochemically active species.

In an alternative detection method embodiment shown in FIG. 11, the electrochemically active properties of the 1-Naphthol reaction product are exploited to produce a measurable detection signal without the use of redox couple. The electrochemical effect of 1-Naphthol can by directly monitored by recording drain current at the potential that favors 1-Naphthol oxidation, and at the same time doesn't facilitate electrochemical reaction between electrolyte and device in the absence of 1-Naphthol (for example Vg=−0.4 V vs. Ag/AgCl). It may be seen that the current initially increases rapidly upon addition of 1-Naphthyl substrate due to the prompt creation of 1-Naphthol. The current then decreases in an exponential fashion as 1-Naphthol is oxidized and begins to suppress electron transfer to the nanotube 14 of device tip 20.

As shown in FIG. 11, the response of the device 10 to 1-Naphthyl substrate exposure is a result of competing processes—the creation of 1-Naphthol by enzymatic action, and the subsequent oxidation and precipitation of the oxidized 1-Naphthol on the nanotube network. The Properties of the signal plotted in FIG. 11 include features which may be readily analyzed, based on appropriate calibration, correlated to target concentration, and used to determine the analyte concentration in a operational sample. For example, the rate of rise of drain current is related to enzyme amount, which is in turn a function of bound target. The peak current magnitude is related to the point at which the current suppression effect of the oxidized product dominates over the electrochemically active properties of the 1-Naphthol. Finally, the rate of current suppression following peak current (e.g., exponents and time constants of decay) may be analyzed.

Comparison of Carbon Nanotube Electrode with Conventional Electrode Materials.

Figure 12:
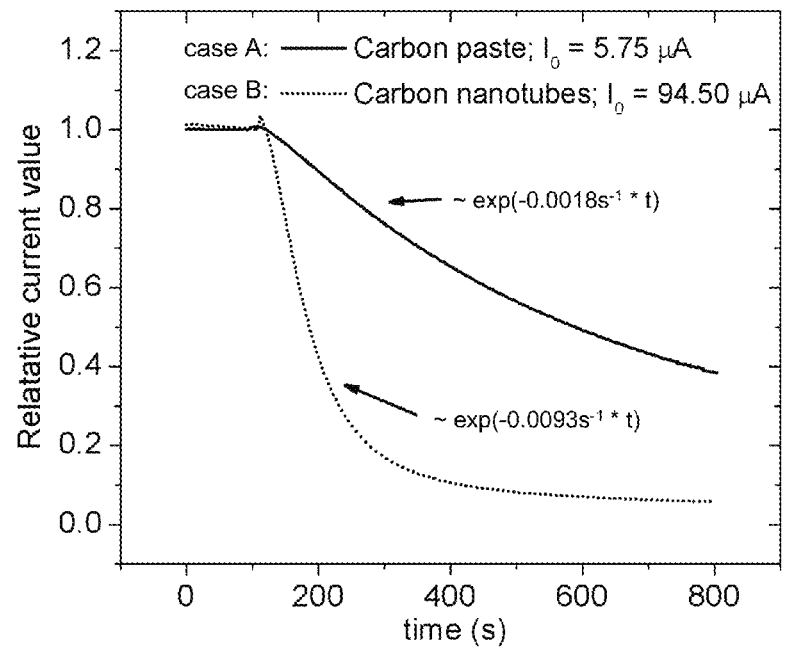
FIG. 12 is a plot comparing the relative activity of a device such as shown in FIG. 1 with a similar device substituting a carbon paste electrode material.

FIG. 12 show a comparison of a sensor device such as described above with respect to FIG. 1 with an alternative sensor device employing carbon paste (case A) in substitution for the carbon nanotube network 14 included in tip 20 of device 10 in FIG. 1 (case B).

The comparison highlights the advantages of including an electrode comprising carbon nanotubes, especially when configured as a random interconnecting network. Similar comparisons of a CNT electrode with a gold film electrode show an even greater advantage in employing carbon nanotubes.

For purposes of the comparison, both the carbon paste electrode (case A) and the carbon nanotube network electrode (case B) were configured to have a surface area of about 1.5 cm$^2$. The otherwise comparable devices were exposed to a buffer comprising 100 mM Tris HCl, 1 mM ZnCl2, 1 mM MgCl2, pH 8), the buffer also including 20 mM Fe(CN)$_6^{-3/-4}$ (redox couple) and 2 mM 1-Naphthyl (reporter substrate).

Signals were then measured of the square wave voltammetry current with Vg=−0.25 vs. Ag/AgCl, the measured current being normalized by its value at the time of enzyme injection (alkaline phosphatase 2 μg/ml) at t~110 s. The results for the carbon paste electrode (Case A) are shown as a solid curve, and the results for carbon nanotube network electrode (Case B) are shown as a dashed curve.

As may be seen in FIG. 12, the carbon nanotube network electrode had more than a 16 fold higher current value prior to current suppression: 94.50 versus 5.75 (microAmps), and likewise showed a much faster current suppression response following enzyme injection, as demonstrated by a more than 5 fold larger exponent constant magnitude: about exp(−0.0093 s$^{-1}$*t) versus about exp(−0.0018 s$^{-1}$*t). It is believed that these differences may be attributed, at least in part, to the large surface area of the nanotubes of the interconnecting network, and to the chemical property of the product of enzymatic reaction (1-Naphthol) tending to interact strongly and bind to carbon nanotubes so as to induce current suppression.

Alternative Sensor System Architectures

FIGS. 13A-13B show an alternative sensor embodiment functionally similar to that shown in FIG. 8, having an alternative geometric arrangement. For purposes of comparison, the same reference numerals are used to identify elements. The device comprises a sensor substrate 12 (e.g., comprising PET, polycarbonate, flexible polymers, or the like) having a reaction or sensor tip portion of its surface 20 on which an interconnecting carbon nanotube (CNT) network 14 is disposed. The conductive trace 15 is formed in a circular configuration disposed upon network 14 (alternative configurations may be used). Encapsulation layer 16 covers portions of both trace 15 and network 14. A central aperture in both trace 15 and layer 16 leaves a portion of network 14 exposed.

As in the embodiment of FIG. 8, the example shown in FIGS. 13A-13B includes an enzyme complex 40 having one or more binding species (e.g., antibodies 42) linked to a reporter enzyme (e.g., alkaline phosphatase 31), the binding species having specificity for analyte 23.

FIG. 13C shows schematically an alternative embodiment of an enzyme complex having multiple enzyme groups linked together, so as to enhance reporter substrate activity. Enzyme complex 50 includes a carrier structure 51 to which are linked a plurality of enzyme species 31 (e.g., alkaline phosphatase) and one or more analyte binding species 42 (e.g., an antibody specific for a target analyte). The carrier structure 51 may include, for example, one or more carbon nanotubes, biopolymers, or the like. The enzyme species 31 may be linked to carrier structure 51 by a binding group such as antibody 52. As in the example of FIG. 8, enzyme complex 50 may be immobilized on a sensor 20 by forming a capture probe/target/enzyme complex, which in turn reacts with a reporter substrate. In this example, each target analyte may trigger the activity of a plurality of enzyme species on the available substrate, so as to enhance sensor response and sensitivity.

Label-Free Electrochemical Impedance Spectroscopy

The relative effects of the examples of reporter enzyme/substrate combinations described in the forgoing Examples 1-3 may be compared to label-free or reporter-free alternative methods of detection, using a generally similar device architecture.

The architecture shown in FIG. 1 may be viewed as a capacitor, where the nanostructured electrode (CNT network 14) serves as one plate of the capacitor. When a gate or reference electrode 18 is immersed into a liquid electrolyte also in contact with network 14, an electrochemical double layer is formed between the network and the electrolyte which serves as the dielectric layer of a capacitor. The capacitor voltage is controlled as a function of the applied reference electrode potential.

FIG. 14 shows the equivalent circuit of the device 10 (FIG. 1) shown by the Randel model, where faradic and capacitance processes are represented. See for example A J Bard and L R Faulkner, *Electrochemical Methods: Fundamentals and Applications* (Wiley and Sons, New York, 2001), which publication is incorporated by reference. $C_t$ is the total capacitance (quantum and double-layer capacitances in combination); $R_s$ is the electrolyte resistance; and $Z_f$ is the frequency dependent complex impedance associated with faradic (non-capacitive) processes.

Although the detectable effect is smaller than in other embodiments, in certain embodiments of sensor devices having aspects of the invention, a capture species (e.g., oligonucleotide 26 in FIG. 4 or antibody 22 in FIG. 8) may be immobilized on network 14, so as to capture an analyte species (e.g., polynucleotide 27 in FIG. 4 or antigen 23 in FIG. 8), whereby the capture of the analyte species produces a detectable change in the impedance, capacitance and electrolytic resistance characteristics of the device, without the enhancements of additional labels or reporters, so as to provide label free detection.

Conduit Sensor System Architectures

FIGS. 15A-B shows an alternative lumen-like sensor system embodiment 150 having aspects of the invention, FIG. 15A being a longitudinal section along line AA in FIG. 15B, and FIG. 15B being a cross section along line BB in FIG. 15A The elements of the embodiment are similar in certain respect to the elements shown in FIG. 1. In this example, the substrate 152 is configured to partially or completely enclose a sample volume 159, for example having the shape of a tube or lumen. A nanostructure element 154, (in this example comprising a network of carbon nanotubes), is disposed on or adjacent the inner surface of lumen 152. A contact 155, such as a metallic layer, communicates with network 154 and connects to measurement circuitry (represented by lead 153). A layer of passivation material (such as a dielectric such as SiO2, a polymer, or the like) may be included covering the portion of contact 155 within lumen 152 so as to isolate the contact from the sample volume 159. The substrate lumen may by mounted so as to communicate with sample medium flowing within a fluidic system, here represented by upstream and downstream connectors 157 and 157' providing for a flow of sample medium and other fluids employed in measurement methods having aspects of the invention, as indicated by longitudinal arrows. A counter or gate electrode 158 may be disposed so as to contact the sample medium lying within volume 159. In this example gate electrode 158 includes a portion longitudinally disposed approximately at the center of lumen 152, and is in electrical communication with measurement circuitry via lead 153'.

FIGS. 16A-B shows an alternative conduit sensor system embodiment 160 having aspects of the invention, FIG. 16A being a longitudinal section along line AA in FIG. 16B, and FIG. 16B being a cross section along line BB in FIG. 16A. In this example, substrate 162 is generally planar, although it need not be flat, other shapes being possible.

Substrate 162 may advantageously have an internal surface configured with longitudinal ridges 162', configured to increase the exposed surface area of the substrate 162 relative to the sample volume 169. A nanostructure element 164, (in this example comprising a network of carbon nanotubes), is disposed on or adjacent the inner surface of substrate 162, generally taking the shape of the ridges 162'. A contact 165, such as a metallic layer, communicates with network 164 and connects to measurement circuitry (represented by lead 163). A layer 166 of passivation material may be included covering the portion of contact 165 within lumen 162 so as to isolate the contact from the sample volume 169. The substrate may be mounted to a conduit structure, in this example represented by upper cover 167 spaced apart from substrate 162 by spacers 167' and 167", so as to enclose a sample volume 169. The sensor 160 may communicated with sample medium flowing within a fluidic system, as indicated by longitudinal arrows. A counter or gate electrode 168 may be disposed so as to contact the sample medium lying within volume 169. In this example gate electrode 168 is configured to include a plate disposed on or adjacent upper cover 167, and is in electrical communication with measurement circuitry via lead 163'.

FIG. 16C shows schematically one possible stacked array or matrix mounting of sensor systems having aspects of the invention. A plurality of sensors (e.g., sensors 160a-160f) may be disposed to communicate with a common fluidic system 160'. Alternative embodiments may include sensors mounted in parallel or in series or both (e.g., sensors 160a-c configured in a first series, in parallel flow to 160d-f configured in a second series. In this example, sample (and/or other measurement method fluids) are shown flowing from an inlet volume 169 to an outlet volume 169'. It should be understood the fluidic system 160' may include valves, pumps, reservoirs, waste gates, capillary medium, and the like, to control the direction, rates, sequence, composition and properties of fluid flow and the like. Fluidic system 160' may include active elements, such as filters, sample processors, heaters, coolers, concentrators and the like. The functionalization or capture species of the plurality of sensors (e.g., 160a-160f) may be selected for generally the same specificity, or may be selected to have specificity to different target analytes, for different reactivity or sensitivity to the same target analyte, or combinations of these.

Microprobe Sensor System Architectures

FIGS. 17-21 show a number of exemplary embodiments of a microprobe sensor systems having aspects of the invention. In the examples of FIGS. 17-19, the microprobe sensors are configured as resistive or transconductance sensors (optionally as a transistor). In the examples of FIGS. 20-21, the microprobe sensors are configured as electrochemical sensors, comparable in a number of respects to the embodiment shown in FIG. 1. Combinations of these configurations are also possible.

FIG. 17 shows resistive or transconductance microprobe sensor 170 comprising a central substrate 171, which may be configured as an elongate fiber, rod-like structure, tubular structure or the like. One or more contacts may be deposited adjacent substrate fiber 171, for example as circumferential layers or rings of metallic material, a spaced-apart source and gate pair of contacts 172 and 173 are shown. Optionally, a gate electrode, counter electrode, and/or other electrode may be included, a submerged or isolated bottom gate 175 is shown in this example, disposed to have a portion between contacts 172 and 173. Elements 172, 173 and 175 may communicate with measurement and/or signal transmission circuitry by suitable conductive leads (not shown).

A nanostructure element is disposed on or adjacent to substrate fiber 171. In this example, the nanostructure element comprises a carbon nanotube network 174 spanning to communicate between contacts 172-173. This may be deposited or formed by any of the methods describe herein. In certain embodiments, the network 174 may be conveniently formed by dipping a portion of substrate fiber 171 in a solvent having suspended or dissolved nanoparticles or nanotubes, so as to deposit an interconnecting network upon solvent evaporation.

FIGS. 18A-H show an exemplary sequence of steps for the making of a microprobe sensor 170 generally of the form shown in FIG. 17, the steps enumerated below corresponding to the indicated Figure:

A. A gate electrode 175 may be deposited on a substrate fiber 171, configured to cover a portion of the fiber 171. In this example, fiber 171 may have a proximal probe end (lower portion in figures) and a distal terminal end (upper portion), and gate 175 includes a lead portion 175' extending longitudinally along fiber 171 towards a distal terminal end of fiber 171. Note in alternative embodiments, fiber 171 may have one or more conducting portions (such as a dielectrically coated conductive fiber, a composite fiber, a "bundle" fiber structure with internal leads, or the like) which may be employed as a contact or gate electrode and lead.

B. A gate isolation layer 176 may be deposited covering gate 175, including at least an adjacent portion of the lead portion 175'. Layer 176 preferably is thin, and may have low K properties, so as to maximize the gate capacitance influence. Preferably, layer 176 is formed by ALD methods, of a material such as aluminum oxide, or the like.

C. A contact 173 may be deposited proximally to gate 175, having a lead portion 173' extending above isolation layer 176 and extending longitudinally along fiber 171 towards a distal terminal end of fiber 171, lead portion 173' being isolated from both gate 175 and gate lead 175'.

D. A lead passivation layer 177 may be deposited covering a proximal portion of lead 173'.

E. A contact 172 may be deposited distally to gate 175, having a lead portion 172' extending longitudinally along fiber 171 towards a distal terminal end of fiber 171, lead portion 172' being isolated from both gate 175, gate lead 175', contact 173 or lead 173'. In the example shown, leads 172', 173' and 175' extend at distinct and separate circumferential portions so as to not intersect one another.

F. A lead passivation layer 178 may be deposited covering a proximal portion of lead 172'.

G. A nanotube network 174 may be deposited (optional trimmed following deposition) so as to cover a proximal portion of fiber 171, the network 174 disposed so as to electrically communicate with contacts 172 and 173 while being isolated from both gate 175 and gate lead 175'. Note that the nanotube network (or other nanostructured element) may be suitably functionalized for analyte specificity and/or sensitivity, such as be capture or recognition species, as described elsewhere in this application.

H. Contact passivation layers 179 and 179' may optionally be deposited so as to cover both contacts 172 and 173 so as to prevent exposure to sample medium.

FIG. 19 shows an alternative embodiment of resistive or transconductance microprobe sensor 190, having generally similar elements as the sensor 170 shown in FIG. 17, but having a generally "outside-in" tubular arrangement. Elongate substrate 191 may have a tubular shape and central lumen. In this example, source and drain contacts 192-193, as well as optional gate electrode 195 (and isolation layer, if needed), are disposed on the inside surface of the tubular substrate 191. Nanotube network 194 (or other nanostructured element) is deposited adjacent the inside surface so as to communicate with contacts 192-193.

FIG. 20 shows microprobe sensor 200 configured to suit electrochemical detection methodology, and includes elements comparable in a number of respects to the embodiment shown in FIG. 1. The probe 200 comprises a central substrate 202, which may be configured as an elongate fiber, rod-like structure, tubular structure or the like.

A nanostructure element 204, in this example comprising carbon nanotube network, is disposed to cover a portion of substrate 202, preferably at or adjacent to a proximal end of substrate 202 (lower end in the figures). This may be deposited or formed by any of the methods describe herein. In certain embodiments, the network 204 may be conveniently formed by dipping a portion of substrate fiber 202 in a solvent having suspended or dissolved nanoparticles or nanotubes, so as to deposit an interconnecting network upon solvent evaporation. Note that the nanotube network (or other nanostructure element) may be suitably functionalized for analyte specificity and/or sensitivity, such as be capture or recognition species, as described elsewhere in this application.

The network 204 communicates with at least one contact 205', shown covered with a passivation layer 206, and having a distally extending lead portion 205. A number of alternative operational mountings and installations of microprobe 200 are possible. In the example shown in FIG. 20, the proximal end of probe 200 is arranged to protrude with clearance into the interior volume of a circumferential ring gate electrode 208 (phantom lines) so as to define an intervening space for sample medium or fluid. Both contact 205 and gate electrode 208 (and optional reference electrode and/or other electrodes) may be connected to suitable measurement and/or signal transmission circuitry (not shown).

Note that in alternative embodiments, a gate electrode may be included in the structure of microprobe 200, such as a parallel longitudinal strip deposited along fiber 202 and electrically separated or isolated from contact 205 and network 204.

FIGS. 21A-F show an exemplary sequence of steps for the making of a microprobe sensor 200 generally of the form shown in FIG. 20. Conventional techniques, such as photolithography, vacuum thermal deposition, sputtering and the like, may be used to form the elements described.

In applications directed to low-cost or disposable sensors, it may be advantageous to form or deposit elements by exposure of a proximal portion of an elongate substrate fiber or rod to deposition fluid or environment, such as by dipping in an electro-deposition fluid, nanotube suspension fluid or the like, as is suited to the exemplary steps illustrated in FIGS. 21A-F as follows:

A. An elongate substrate or fiber 202 is provided, such as by extrusion of a polymer or other material.

B. In the example shown, a contact lead portion 205 is formed first (e.g., from metal, graphite, conductive polymer, and the like), extending longitudinally along fiber 202. For example, lead 205 may be formed during extrusion of a fiber 202.

C. Contact base region 205' is formed on a proximal region of fiber 202 in contact with lead 205. In the example shown, contact base region 205' covers the proximal end of fiber 202. In alternative examples, base region 205' may extend also to a distal end of fiber 202.

D. A passivation layer 201 may be deposited covering a proximal portion contact 205'. In alternative examples, passivation layer 201 may be omitted, and the contact 205' does not extend to the proximal end of fiber 202. In other examples, a proximal portion of contact 205' may be removed following deposition. In yet another example, substrate fiber 202 may be composed, in all or part, of a conductive material serving as contact 205', and passivation layer 201 may submerge a proximal portion of conductive substrate 202.

E. A nanotube network 204 may be deposited (optional trimmed following deposition) so as to cover a proximal portion of fiber 202, the network 204 disposed so as to electrically communicate with contact 205'.

H. Contact passivation layers 206 may optionally be deposited so as to cover contacts 205', so as to prevent exposure to sample medium.

EXAMPLE 4

Capture Functionalization Separate from CNT Detector Electrode

A sensor having aspects of the invention may have capture functionalization dispose independently of a detector electrode, such as network 14 as shown in FIG. 8, described above. Embodiments so arranged may employ any of the detection process described above. For example, capture species 22 in FIG. 8 (or an equivalent molecular structure) may alternatively be disposed elsewhere in the sensor system. Such arrangement of these elements permits the function of a detector element, such as network 14, without any effects of physical proximity or contact with capture species 22.

Figure 22:
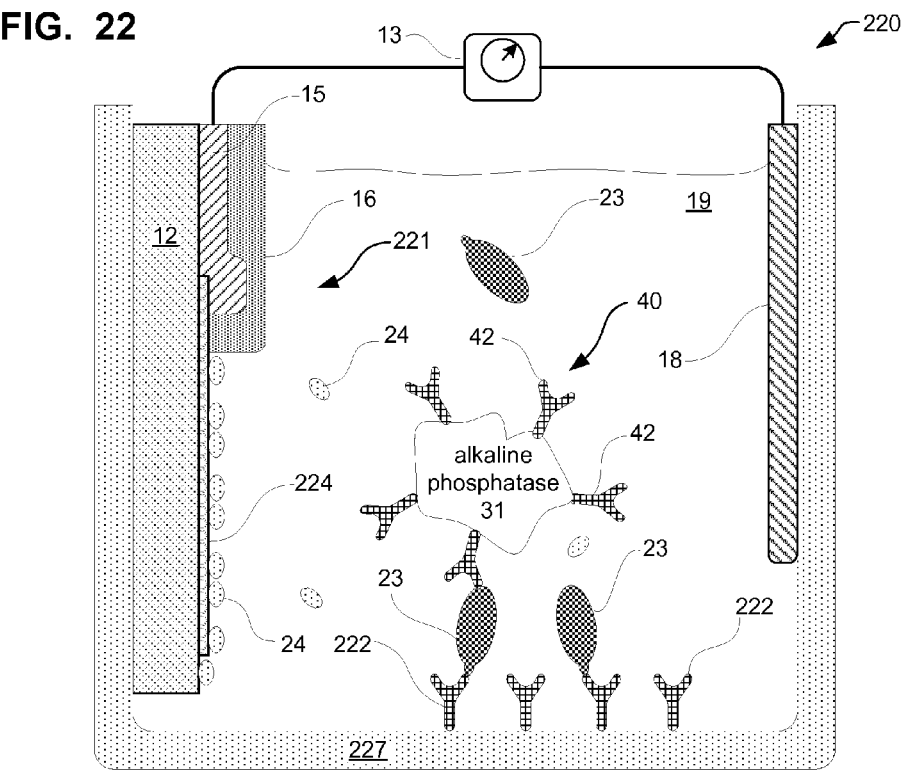
FIG. 22 shows one exemplary embodiment of a sensor system configured for protein detection by faradic current suppression, and having capture species disposed apart and separate from a CNT detector surface or film.

FIG. 22 shows one exemplary embodiment of a sensor system 220 configured for protein detection by faradic current suppression. Generally similar alternative embodiments may be configured for the detections of other types of analyte species, for example employing capture species comprising one or more biological or synthetic molecules having an affinity for a target analyte, such as a polynucleotide probe, an aptamer, a receptor or a ligand. A number of elements of system 220 have generally similar functions and reference numbers as corresponding elements shown in FIGS. 1 and 8.

Sensor system 220 comprises a vessel, container or well 227 holding buffer or fluid media 19 in which both sensor tip portion 221 and a gate electrode 18 are immersed. Sensor tip 221 includes nanotube network 224 in electrical communication with measurement circuitry 13, which in turn is in communication with gate electrode 18. Capture species 222 (e.g., antibodies with target analyte affinity) are disposed apart from network 224, in this example absorbed or bonded (e.g. via ligands or attachment species) to a wall of well 227. As in the example shown in FIG. 8, target analyte species 23 (e.g., a soluble protein species) are permitted to bind to capture species 222.

Buffer 19 may optionally be rinsed following analyte capture, and replaced as described above with respect to other examples. This is particularly valuable where a sample medium (e.g., whole blood) may include constituents interfering with detection.

A reporter enzyme complex 40 may comprise a reporter enzyme 31 (e.g., alkaline phosphatase) bound to one or more binding species 42. As may be seen, an analyte species 23 may bind to both capture species 222 and binding species 42 so as to form an device/analyte/enzyme complex. A reporter substrate (e.g., 1-Naphthyl) may then react with the reporter enzyme to form a product 24 (e.g., oxidized 1-Naphthol), which in turn is absorbed or deposited on network 224, so as to cause a detectable change in properties and produce a signal measurable via circuitry 13.

Figure 23:
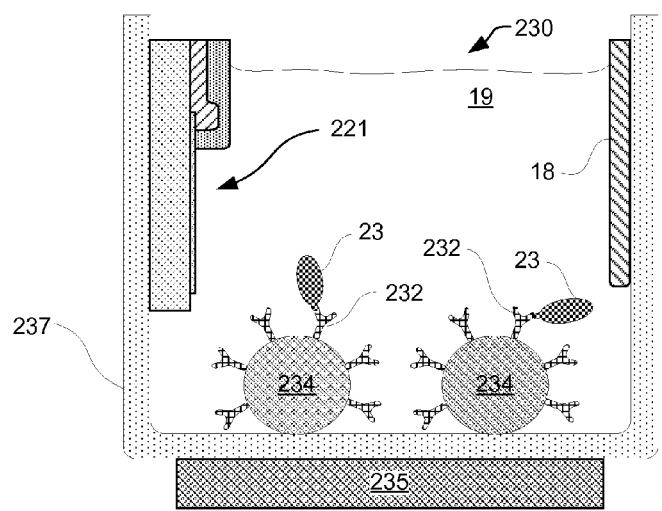
FIG. 23 shows one exemplary embodiment of a sensor system generally similar to that of FIG. 22, configured to employ magnetic bead purification and/or separation methods.

FIG. 23 shows an alternative exemplary embodiment of a sensor system 230 configured for magnetic bead purification and/or separation methods, having functional elements generally similar to the example of FIG. 22. Sensor tip 221 and gate electrode 18 are disposed in contact with fluid medium 19 in well 237. Capture species 232 are bound or linked to magnetic beads 234, so as to permit a large surface area available for analyte capture. Immobilization magnet 235 permits beads 234 to be retained during rinsing and fluid replacement steps.

Figure 24:
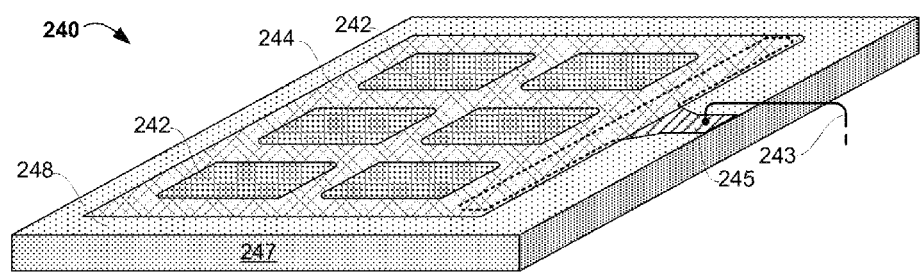
FIG. 24 shows an exemplary embodiment similar in a number of respects to the embodiment shown in FIG. 22, configured to have a grid-like pattern of electrode and capture regions disposed on a substrate.

FIG. 24 shows an exemplary embodiment 240 having aspects of the invention and similar in a number of respects to the embodiment shown in FIG. 22, configured to have a grid-like pattern of electrode regions 244 and capture regions 242 disposed on a substrate 247, the regions 242, 244 configured so that capture regions 242 are adjacent to but separate from electrode regions 244.

As employed for biomolecule detection by faradic current suppression as described above with respect to FIGS. 8 and 22, the embodiment 240 may be exposed to an analyte sample and detection measured employing a buffer gate electrode. A reporter enzyme complex and reporter substrate (not illustrated) may be employed to produce an analyte-triggered enzymatic reaction product in region 242 which diffuses to be absorbed on region 244, so as to produce a detectable signal.

Substrate 247 may advantageously include an insulating polymeric material, e.g., a PET sheet material. Electrode region 244 may comprise a CNT network, e.g., deposited by spray deposition or the like on substrate 247. In alternative embodiments, electrode region 244 may be formed by CVD or PECVD, for example, on a quartz or silicon substrate. Capture regions 242 may comprise a plurality of antibodies selected to have an affinity for a target analyte, bound to or absorbed on the substrate 247. In alternative embodiments, capture regions 242 may comprise one or more other biological or synthetic molecule having an affinity for a target analyte, such as a polynucleotide probe, an aptamer, a receptor or a ligand.

A conductive trace 245 (e.g., comprising a conductive ink, conductive polymer layer, deposited metal, or the like) may be included to communicate with at least a portion of the electrode region 244, and to permit a signal or current to be conducted to measurement circuitry via lead 243 (circuitry components, buffer fluid, and the like are not shown in FIG. 24, see FIG. 22, for example).

Note that CNT electrode 244 may be deposited or formed either before or after trace 242. Likewise, conductive trace 242 may be disposed above, beside or below CNT electrode 244. As describe above with respect to FIGS. 1, -5 and 8, the conductive trace may be coated or passivated (not shown) so as to isolate from exposure to a sample medium.

Substrate surface 248 may be coated or treated, for example with a dielectric material, a protective material, a material to assist or accomplish binding of a capture species, and the like. For example, known methods may be used for attaching a capture antibody to a polymeric substrate.

Figure 25:
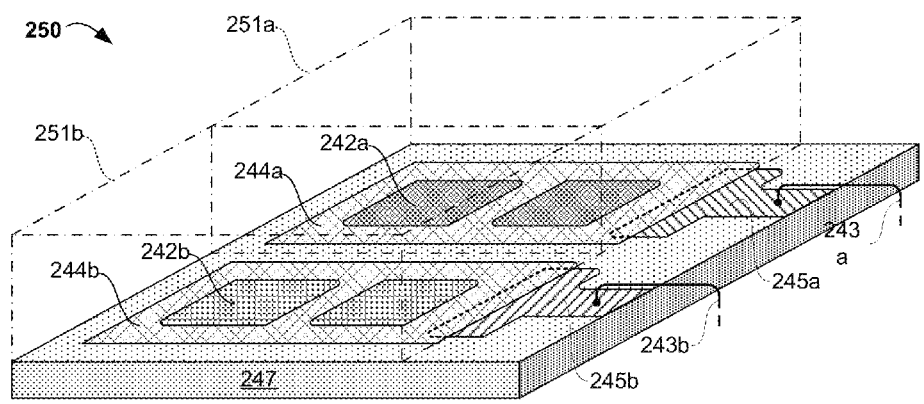
FIG. 25 shows an alternative exemplary embodiment generally similar to the embodiment shown in FIG. 24, configured as an array to measure two or more analytes in a sample.

FIG. 25 shows an alternative exemplary embodiment having aspects of the invention and generally similar to the embodiment shown in FIG. 24, configured as an array to measure two or more analytes in a sample by distinct detection signals for each analyte. The reference numerals are generally the same as in FIG. 24 where functions are comparable.

In the example of FIG. 25, the system 250 comprises two or more distinct space-apart electrode regions 244a, 244b, each disposed adjacent a corresponding distinct capture region 242a, 242b respectively. Capture regions 242a, 242b may be functionalized with different capture species having affinity for the different target analytes. Likewise, conductive traces and circuitry leads 243a, 245a are distinct and separated from corresponding elements 243b, 245b.

Application of a sample may be made simultaneously to each such region so as permit analyte-specific capture from a sample in each region 242a, 242b. System 250 is configured so as to prevent or minimize subsequent cross-sensitivity due to a reporter product produced in region 242a being absorbed on region 244b, or vice versa. This may be provided by isolation structures 251a, 251b (e.g., distinct wells, fluidic passages, barriers and the like). Alternatively, the spacing, dimensions, diffusion properties and capillary flow materials and the like (e.g., in a disposable test strip embodiment) may be optimized or configured to avoid or minimize detection signal interference.

One of ordinary skill in the art will appreciate that a number of fluid movement and control methods may be applied to the examples of FIGS. 22-25 without departing from the spirit of the invention. For example, microfluidic system or test strip systems having capillary fluid movement mechanisms may be employed to perform capture, rinse/separation, and reporter enzyme/substrate application steps.

EXAMPLE 5

Amperometric Detection by Electrochemically Active Reporter

In addition or alternative to measurements performed by methods described above employing variable potential between a nanotube electrode and a counter or reference electrode (e.g., cyclic voltammetry; square wave voltammetry, and the like), sensor devices having aspects of the invention can give sensitive detection performance at a constant potential (amperometric). In certain exemplary embodiments, a constant potential may be employed so as to reduce or eliminate background noise in a signal, which may be due to cross reactivity or interference by electro-active species in a sample. At a constant potential, a device may be equilibrated to the measurement environment prior to addition of a reporter substrate, so that electro-active interference currents tend to die out.

Figure 26:
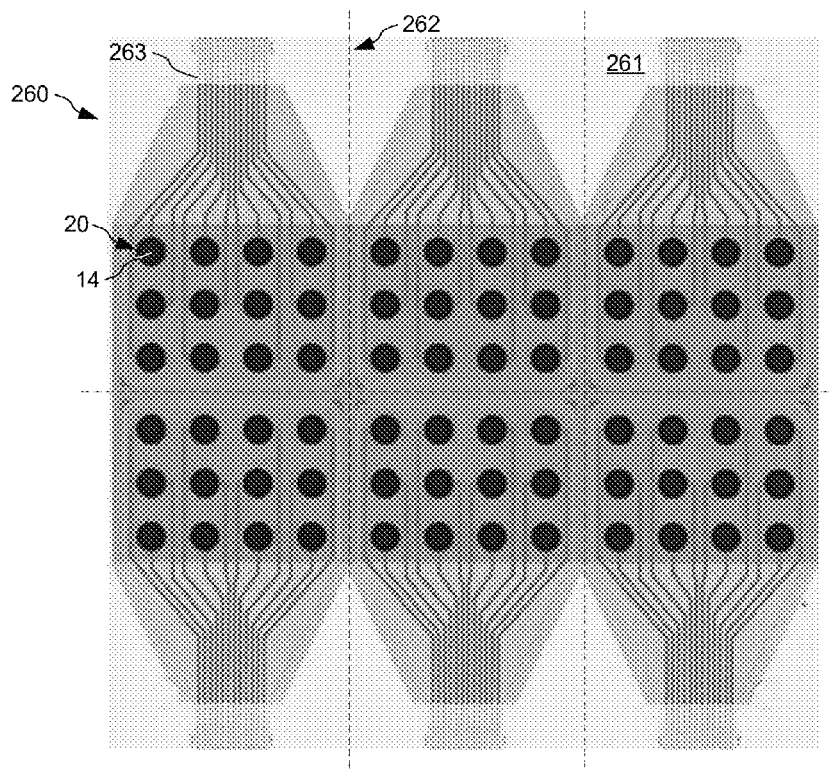
FIG. 26 shows an array of devices having aspects of the invention, generally similar to that shown in FIGS. 13A, 13B and FIG. 8.

FIG. 26 shows an array 260 of substantially identical devices 20 generally similar to that shown in FIGS. 13A-B and also FIG. 8. The devices may be advantageously prepared on a sheet substrate 261 by screen-printing methods (e.g., using metallic and/or carbon inks, polymer sheet substrates, polymer encapsulation and protective layers and the like). The substrate 261 may be cut following device construction to separate panels 262 with a selected number of devices 20 (e.g., 12 devices per panel). Leads 263 may conveniently extend to a panel margin to facilitate connection to measurement circuitry.

In this example, the sensor device 20 includes an electrode 14 comprising a carbon paste base layer deposited on a polymer substrate, and coated with a layer of carbon nanotubes by solution deposition, in this case employing hydrophilic carboxylated SWNT deposited from dilute aqueous solution (other solvents and CNT types may be used), resulting in a network including about 1 microgram of nanotubes in the device.

In this example, streptavidin was employed as a sample analyte, and the network 14 of device 20, and the network 14 was functionalized with a capture species (22 in FIGS. 13A-B) comprising polyclonal anti-streptavidin (a-SAv) antibodies, absorbed onto network 14 from a phosphate-citrate buffer (PCB). An second substantially identical sensor device was employed as a control, and was similarly functionalized with a capture species comprising anti-hCG antibodies, deposited in the same fashion. Following functionalization, the detection and control devices were washed with a rinsing buffer (phosphate buffered saline pH 7.4 containing 0.05% Tween 20 (PBST). Following functionalization, the devices were coated to inhibit non-specific binding (24 in FIGS. 13A-B) by exposure to "Casein Blocker" from Pierce Inc. (1% Casein in PBS+0.1% Kathon preservative).

Functionalization of devices such as shown in FIG. 26 may conveniently be performed using automated micropipette applicators, which can precisely position droplets of reagents in microliter quantities upon the network electrode 14 of each device 20. This also conveniently permits a spectrum of functionalization of devices of an array 262.

The analyte species employed in was streptavidin, in this example conjugated with enzyme horseradish peroxidase or SA-HRP, (analyte 23 and enzyme reporter complex 40 in FIG. 8). In the examples shown in FIGS. 26A-B and 27, a sequence of 10 "target" dilutions was prepared comprising SA-HRP diluted in Casein Blocker, including a zero control sample, and 9 concentrations ranging from 0.1 ng/ml up to 667 ng/ml.

The series of generally identical devices were exposed to one of the target dilutions, and thereafter washed with PBST. The devices were then exposed to an measurement buffer comprising 90% PCB, 10% DMSO, 0.1 mg/ml TMB or Tetramethylbenzidine (TMBB), and subjected to a constant potential, relative to a of reference electrode (Ag/AgCl), of −0.1 V. The devices were permitted to equilibrate for a period of time (minutes) prior to addition of the substrate ($H_2O_2$, hydrogen peroxide) at a buffer final concentration of 2 mM. As shown in FIGS. 26A and 26B, the current level closely approaches a zero value during equilibration.

Figure 27A:
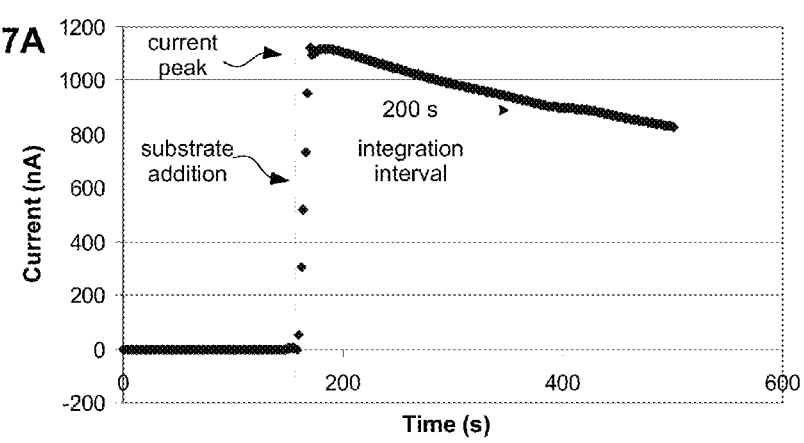
FIGS. 27A and 27B show an analyte response plot and a zero reference plot respectively for a devices such as shown in FIG. 26, employed for analyte detection at constant potential.
Figure 27B:
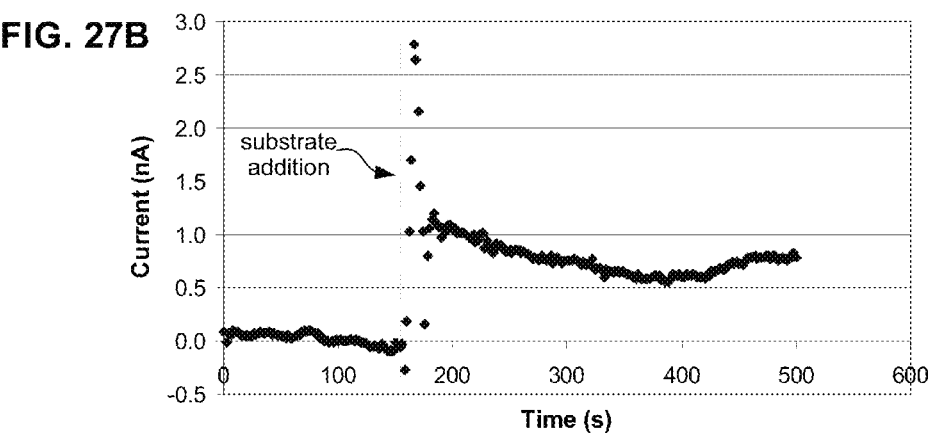
Figure 28:
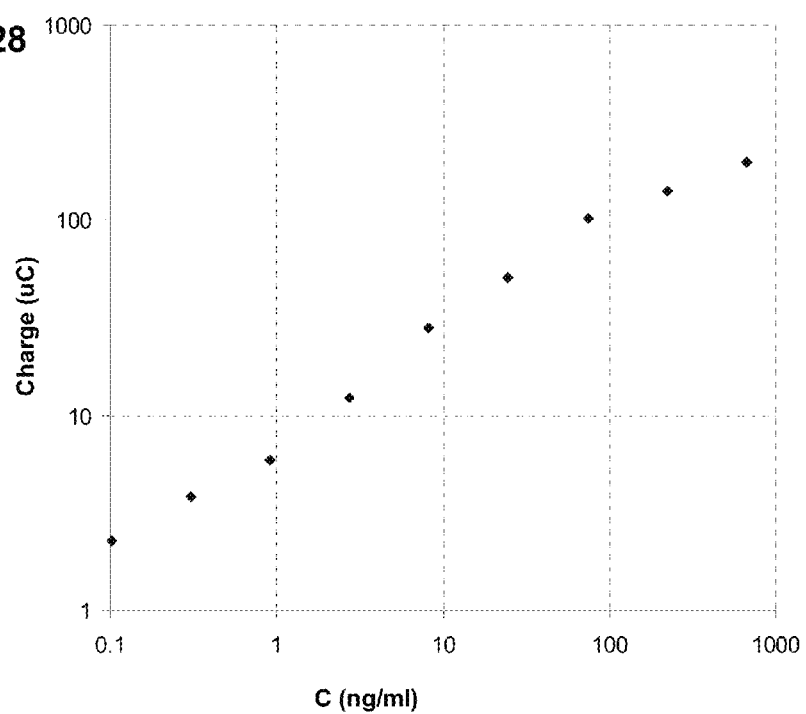
FIG. 28 shows a calibration plot for detection as in FIG. 27A, for a range of analyte concentrations.

FIGS. 27A-B and 28 illustrates measurements made employing an exemplary embodiment as described above. FIG. 27A illustrates the device response for the SA-HRP dilution at a concentration of 667 ng/ml. As shown in FIG. 27A, measurements indicative of analyte concentration may include one or more of alternative electrical characteristics of the device, such peak current level, rates of change of current, and the like. In this example, current produced by the device was integrated for a predetermined period following substrate addition (200 s).

FIG. 27B shows a comparative response of the zero concentration sample, which may be seen to be generally 3 orders of magnitude lower than the 667 ng/ml example of FIG. 26A, demonstrating high selectivity of the response.

FIG. 28 is a calibration plot showing the observed (200 s integration) charge flow produced by the 9 target dilutions, using substantially identical devices as described above, shown log-log plot. Without being limited to theory, it is believed that the reaction mechanism is thought to be the following: the HRP enzyme bound to target (SA) converts $H_2O_2$ to water and after that reacts with TMB so as to donate an electron to HRP, producing the oxidized form TMB+. The nanotube electrode 14 is at such potential that it is able to donate an electron to TMB+ to reduce it back to TMB, thus generating the observed current. The current is correlated with the number of SA-HRP molecules bound to the device and that's how the calibration curve is produced. The magnitude (and integral) of the current is correlated with the number of SA-HRP molecules bound to the device, and thus to target concentration.

One of ordinary skill in the art will understand that the methods described in this example may be readily applied using selected reporter enzymes and capture species (e.g., antigens, antibodies, oligonucleotides and the like) so as to functionalize sensor 20 for any one of a wide range of analytes species.

EXAMPLE 6

Dual-Path Nanoelectronic Assay Device

Exemplary embodiments having aspects of the invention include assay devices employing capillary or sorbent migration membranes for provision of analyte sample and reagent to one or more sensors. Such assay devices are suited to, among other things, the practice of the electrochemical biomolecule detection methods and sensors described herein.

An assay device is described in U.S. Pat. No. 7,189,522 entitled "Dual Path Immunoassay Device", which patent is incorporated by reference herein. The devices described in U.S. Pat. No. 7,189,522 generally appear to employ color-marked conjugates to express a visible test line indicative of the presence of a sample ligand. The devices utilize antigen-antibody reactions to complex a conjugate delivered to the test line along a first sorbent migration membrane path with a sample ligand delivered to the test line along a second sorbent membrane path, the complex defining a visible line at a location having immobilized test antigen or antibody material printed on or affixed to the one of the membranes. These devices require separate application ports for each of sample and conjugate solution, they require optimally timed application of each material at a respective port to function effectively, and they produce solely a visible indicator on the membrane (e.g., inspected though a window).

In contrast to the devices described in U.S. Pat. No. 7,189,522, embodiments having aspects of the invention are not limited to simply the expression of visible test lines printed or affixed to the sorbent membrane itself, but rather include effective fluidic engagement of capillary or sorbent migration membrane(s) with electrodes of a nanoelectronic electrochemical sensor platform so as to provide a locus for an electrochemical reaction and charge transfer, so as to produce electronic signals which can be communicated to measurement circuitry for analyte detection, measurement and/or for control signals.

Certain embodiments having aspects of the invention include dual or multiple paths for separate delivery of a plurality of distinct reagent materials to the sensor platform at selected times in the detection process. For example, certain embodiments include of a first path for delivery of both a sample (possibly having biomolecule analytes) and for delivery of reporter catalysts (e.g., an enzyme complexed with a capture species), while also including a second path for delivery of a substrate substance.

In addition, certain embodiments having aspects of the invention eliminate the need for a separate input application of test fluids to a sample port and reagent port, and eliminate the need for timed application of these separate test fluids. These embodiments permit simple operation without erroneous or inconsistent results associated with timing variations in application of test fluids.

Assay Device. FIGS. 29 and 29A-29C illustrate a first exemplary embodiment of dual-path nanoelectronic assay device 290 having aspects of the invention, in which FIG. 29 shows the platform of the device 290; FIG. 29A shows a cross section along line A-A in FIG. 29; FIG. 29B shows a cross section along line B-B in FIG. 29; and FIG. 29C shows an exploded detail of the sensor platform 292 of device 290. FIG. 29D shows certain alternative configurations of sensor platform 292.

Device 290 comprises a body 291 having a sensor platform 292, a first opening 293 and a second opening 294. Each opening 293, 294 is spaced a distance apart from sensor platform 292. First opening or port 293 communicates with a proximal end of an first elongate sorbent migration membrane 295. Membrane 295 extends from opening 293 to define a first path within body 291 so as to communicate at a distal end to engage sensor platform 292, the first path providing for migration of applied fluids from opening 293 to communicate with sensor platform 292. Second opening or port 294 communicates with a proximal end of an second elongate sorbent migration membrane 296. Membrane 296 extends from opening 294 to define a second path within body 291 so as to communicate at a distal end to engage sensor platform 292, the second path providing for migration of applied fluids from opening 294 to communicate with sensor platform 292.

In the example shown, body 291 has generally T-shaped upper and lower halves 291a and 291b which are shaped to be superimposed to define conduits 297 and 298 through which membranes 295, 296 extend respectively, but alternative body conformations may be employed without departing from the spirit of the invention. For example, portions of membranes 295 and/or 296 may be exposed on or extend from the surface of body 291 to allow direct application of materials, such as by dipping or drop application, eliminating a discrete port, such as opening 293 and/or 294. In other alternatives, elongate membranes 295, 296 need not be generally orthogonally disposed, but, for example, may be generally parallel, either in opposition or having both proximal ends extending approximately from a common end of body 291 towards sensor platform 292.

Either or both of sorbent membranes 295, 296 may comprise one or more bibulous, fibrous and/or porous material such as nitrocellulose, cellulose acetate, glass fibers, porous polymers, or the like, and may comprise treatment or coatings to alter properties such as hydrophilic/hydrophobic properties. Material characteristics, such pore size or porosity, material composition, or material coatings or treatments may be selected to be different for the first membrane 295 and second membrane 296. Each membrane may be of uniform composition or may have variable composition or characteristics along its length. In certain embodiments, the membranes comprise nitrocellulose fibers, which may have a backing or support layer.

In certain embodiments the pore size (or other material properties or characteristics) of a first membrane are selected so that, where a first fluid has migrated along the first membrane to the sensor platform before any fluid has migrated on the second membrane to reach the sensor platform, the first fluid is inhibited from a great degree of absorption into the second membrane. For example where membranes 295, 296 each comprise a porous nitrocellulose material, the pore size of membrane 295 may be larger (e.g., about 15 microns) than the pore size of membrane 296 (e.g., about 3 microns) so that fluids from membrane 295 will tend not to migrate to a great degree into membrane 296.

In contrast to the devices described in U.S. Pat. No. 7,189,522, the membranes 295, 296 may be configured in length and/or other properties (e.g., pore size, material composition, treatments, additives and the like) so that fluids may be delivered to openings 293 and 294 simultaneously, and migrate so as to reach platform 292 at a selected spacing in time. For example, membrane 296 may be configured to have a selected time-delay relative to membrane 295 (as required for a desired operational method, see example below).

Platform Arrangement. As shown in FIG. 29B and in detail in FIG. 29C., the distal ends of first sorbent membrane 295 and second elongate sorbent membrane 296 are disposed to be clamped between two portions of sensor platform 292, including a working electrode portion 20, and a counter-electrode portion 297. Counter electrode portion 297 includes an exposed electrode 298, which may optionally be a reference electrode (e.g., comprising a reference material such as Ag/AgCl). In this example, membranes 295, 296 are disposed back-to-back, wherein membrane 295 is shown contacting the surface of electrode 14 of sensor portion 20, membrane 296 is shown contacting the electrode 298 of counter-electrode portion 297. The disposition of the electrode portions 14 and 298 is such that membranes 295, 296 make effective fluidic contact with both electrodes and with each other, so as to define a reaction zone between them, and so that fluids migrating in each membrane come in contact with adjacent electrode and membrane surfaces. Preferably the electrode portions 14 and 298 are disposed so as not to prevent fluid migration in the distal ends of membranes 295, 296, for example, by excessive compression.

Electrodes 14 and 298 communicate with respective leads 15a, 15b which extend to permit communication with measurement circuitry (not shown), for example by means of a conventional plug-type connector. Selected regions of working electrode portion 20 and counter-electrode portion 297 may be protected by insulating layers 16 and 299 respectively, so as to prevent contact with fluids transmitted in membranes 295, 296.

Alternative Arrangements. In the example shown, the working electrode portion 20, and counter-electrode portion 297 of sensor platform 292 define a "clamp" arrangement confining and engaging membranes 295, 296 between them, an arrangement which provides for convenient assembly with of device 290. However, alternative sensor platform conformations may be employed, without departing from the spirit of the invention.

For example, as shown in FIG. 29D alternative sensor platform 292' comprises working electrode and counter-electrode portions 20' and 297' which may be disposed side-by-side and electrically-isolated from one another, to define a planar arrangement contacting membranes 295, 296 adjacent an inter-membrane contact region. In this example, working electrode portion 20' includes an electrode 14 disposed at a tip portions of an elongate base 12 (see the examples of also FIGS. 20 and 21A-F), the tip portion of being disposed at an inter-membrane contact region between membranes 295 and 296. Counter electrode portion 297' similarly has an electrode 298 disposed at an inter-membrane contact region. Additional alternative conformations are possible, such as multilayer membranes, tubular or concentric membrane arrangements, and the like, without departing from the spirit of the invention.

Assay device 290 may include additional sensor arrangements for control purposes, reference purposes or for detection of additional analytes. For example, as shown in FIG. 29, sensor platform 292 includes an additional control sensor platform 300 disposed along an control membrane region 301, membrane region 301 disposed distally from platform 292 and in communication (or being an extension of) either or both of membranes 295, 296. Platform 300 is configured to provide a control signal indicating that sample and/or reagents sufficient to perform an effective test have migrated to communicate with platform 292.

In certain embodiments, an additional membrane or reservoir sorbent region 302 is disposed distally of platform 292 (and platform 300 if this is included) so as to provide a wicking reservoir to assist in migration of fluids. Region 302 may include includes a relatively thicker absorbent pad or membrane. In certain embodiments, either or both of openings 293 or 294 may be provided with a deposition pad or filter (pad 303 is shown adjacent opening 293 in contact with membrane 295), to initially hold and distribute applied fluids.

Either or both of membrane 295 or 296 may have a reagent supply region (305 and 306 are shown respectively) along the path of the membrane (and/or in a respective deposition pad (303 is shown) which provide a supply of a selected reagent material, composed so as to dissolve in applied fluids migrating along membrane 295 and/or 296 respectively so as to carry the reagent to the sensor platform 292. In certain embodiments, more than one reagent region may be included sequentially along a membrane path, so as to provide sequential application of species to platform 292.

Note that where a fluid is to be applied (to either opening 293 or 294) without the use of specialized buffer or solvent agents (e.g., application of a neat urine sample), either or both of regions 305 and 306 (or alternatively deposit pads 303 or 304) may contain additional buffering or conditioning materials, to be dissolved in the migrating fluids (e.g., to adjust pH, salinity, or other properties).

Operation Example. The exemplary device 290 is suited to the practice of the various embodiment methods electrochemical biomolecule detection described herein. In an example configured for carrying out a detection method generally similar to those described with respect to FIGS. 8-11, the following steps may be included:

(a) Device 290 is provided connected to measurement circuitry, device 290 being prepared so that electrode 14 (or an adjacent surface) of sensor platform 292 is functionalized with a binding species 22 (e.g. a polyclonal antibody active for an antigen analyte 24) as described above (See FIG. 8). Device 290 is further prepared having a reporter enzyme complex 40 (e.g., polyclonal antibody to antigen analyte 24 bound to alkaline phosphatase 31) impregnated in region 305. Device 290 is further prepared having a reporter substrate (e.g., 1-Naphthyl) and optionally a redox couple (e.g., ferrocyanide/ferricyanide) impregnated in region 306.

(b) A sample possibly containing an analyte species 24, optionally carried in a selected buffer solution (e.g., PBS) is applied to opening 293 so as to absorb and migrate along membrane 295. As a result the sample (and buffer) migrate to region 305, dissolves the reporter enzyme complex 40, and further migrate to platform 292.
  (i) As a further result, analyte species 24 (if present) binds with the capture species 22, and immobilizes reporter enzyme complex 40.
  (ii) In the event that no analyte 24 is present, continued buffer/sample migration carries reporter complex 40 distally beyond platform 292 towards wicking reservoir 302.

(c) After a desired amount of time (which may be zero or an arbitrary delay or may be an optimized delay period), a transport buffer (e.g., PBS) is applied to opening 294, so as to absorb and migrate along membrane 296. As a result the transport buffer migrates to region 306, dissolves the reporter substrate and optional redox couple, and further migrates to platform 292, so as to arrive at platform 290 subsequent to step (b)(i) or (ii).

(d) A selected voltage is applied between electrode 14 and electrode 298 by measurement circuitry (e.g., a voltage equivalent to about −250 mV versus an Ag/AgCl reference electrode), and current signal measurement and/or recordation is initiated.
  (i) As a result, if reporter enzyme complex is immobilized on electrode 14 (or an adjacent surface) by capture species 22 and analyte 24, then electrochemical activity and a detectable current signal is initiated by activity of 1-Naphthyl (optionally enhanced by redox couple). The electrochemical activity is subsequently suppressed as reporter enzyme activity produces Naphthol.
  (ii) In the event that no reporter enzyme complex is immobilized, the selected voltage produces zero or measurably lower electrochemical current signal magnitude, and no subsequent current suppression by substrate/enzyme reaction occurs.

(e) The electrochemical current signal from step (d) is analyzed to determine presence and/or concentration of analyte 24.

Single-Port, Dual-Path Assay Device. FIGS. 30, 30A, and 30B show an example of an alternative embodiment 310 having aspects of the invention, which eliminates the need for a separate input application of test fluids to a sample port and reagent port, and eliminates the need for timed application of these separate test fluids. Among other things, examples such as 310 may be configured for simple user practice, such as is used dip-stick or urine stream type sample application.

FIG. 30 shows the platform of the device 310; FIG. 30A shows a cross second along line A-A in FIG. 30; and FIG. 30B shows a cross second along line B-B in FIG. 30. Where elements of device 310 are generally similar to those of device 290, the same element reference numbers are used as in FIGS. 29, 29A, and 29B.

In the example shown in FIGS. 30, 30A, and 30B, device 310 comprises a body 311 including upper and lower portion 311a and 311b, having a sensor platform 292, and a single opening, port or exposure region 313. Opening 313 is spaced a distance apart from sensor platform 292.

Opening 313 communicates with a proximal end of each of two elongate sorbent migration membrane 315, 316. Like the membranes 295 and 296 of device 290, the membranes 315, 316 of device 310 extend from opening 313 to define two respective paths for migration of applied fluids from opening 313 to communicate so as to engage sensor platform 292.

The sensor platform 292 (and control platform 300) may be configured as in the examples of FIGS. 29, and 29A-29C, or as in the alternatives, such as shown in FIG. 29D. Regions 305 and 306 on or adjacent membranes 315 and 316 respectively may carry or be impregnated with reagents specific to fluids to be delivered to platform 292 by fluids migrating on membranes 315 and 316 respectively.

Differential Migration Intervals. In membranes 315 and 316 may be configured be configured in length and/or other properties (e.g., pore size, material composition, treatments, additives and the like) so that fluid delivered to opening 313 will migrate differentially along membranes 315 and 316 so as to reach platform 292 at a selected spacing in time. For example, membrane 316 may be configured to have a selected time-delay relative to membrane 315.

This migration interval differential functions as a built-in timing function, providing delivery of separate buffer or fluid factions, optionally containing different reagent additions from regions 305 and 306 to sensor platform 292 at a selected time. As described in the "Operation Example" above with respect to device 290, step (c) may be timed as a selected delay without the necessity of a separate application of fluid to a separate port.

The differential migration interval of the device 310 provides both simply user steps and instructions, suitable for patient-administered testing, but also lends itself to convenient application forms, such as dip-stick or urine stream application. Note the opening 313 may comprise an exposed portion of sorbent membrane suitable for placement in a urine stream, as in conventional pregnancy test immunoassay systems, and the like.

CONCLUSION

Having thus described a preferred embodiments and methods of making them, it should be apparent to those skilled in the art that certain advantages of the within system have been achieved. It should also be appreciated that various modifications, adaptations, and alternative embodiments thereof may be made within the scope and spirit of the present invention. For example, specific examples have been illustrated for nanostructured elements comprising a nanotube network, but it should be apparent that the inventive concepts described above would be equally applicable to other types of nanostructured elements. The invention is further defined by the following claims.

The invention claimed is:

1. A method of detecting the presence, concentration or amount of a biomolecular analyte species in a sample using a device or assembly comprising a first capture species immobilized relative to a base, the first capture species configured to have a binding specificity for the analyte; a working electrode disposed in communication with the base, the working electrode configured to provide effective electrical communication with a communicating aqueous fluid; and a catalyst complex including a catalyst fixed to a second capture species, the second capture species configured to have a binding specificity for the analyte, and the catalyst having an activity for a selected reporter substrate to produce a product species, the product species configured to interact with the working electrode so as to produce a detectable change in an electrical property of the working electrode, the method comprising:
    (a) exposing the immobilized first capture species to analyte species present in a sample, under condition sufficient to permit binding of the first capture species to the analyte species so as to immobilize at least some of the analyte species relative to the base;
    (b) exposing the catalyst complex to the analyte species, under condition sufficient to permit binding of the second capture species to the analyte species, so as to bind the catalyst complex to at least some of the immobilized analyte species;
    (c) following carrying out in any operative order the analyte-immobilization operation (a) and the catalyst-complex-binding operation (b):
        (i) removing any unbound catalyst complex; and
        (ii) exposing the immobilized catalyst complex to the reporter substrate under condition sufficient to permit reaction of the reporter substrate with the catalyst to produce the product species; and
    (d) making at least one electrical measurement indicating the change in charge transfer due to the interaction of the product species with the working electrode so as to detect the presence, concentration and/or amount of the analyte species in the sample, wherein the working electrode comprises a nanostructured element including a material selected from the group consisting essentially of graphene monolayers and graphene multilayers and wherein the analyte species comprises an antibody species, and wherein at least one of the first and second capture species comprises an antigen having a binding affinity for the antibody.

2. The method of claim 1, wherein the catalyst includes an enzyme having activity to react with the reporter substrate to produce the product species.

3. The method of claim 1, wherein the detectable change in an electrical property of the working electrode includes a detectable change in charge transfer in an electrochemical reaction in a communicating aqueous fluid sample.

4. The method of claim 1, wherein the first capture species and the working electrode are fixed adjacent the base in proximity to one another, so as to permit the product to be communicated to the working electrode by molecular diffusion.

5. The method of claim 4, wherein the first capture species is fixed to the working electrode.

6. The method of claim 1, wherein the device or assembly further comprises a counter electrode or a reference electrode.

7. The method of claim 3, wherein the making at least one electrical measurement of operation (d) includes measurement of electrochemically induced faradic current.

8. The method of claim 7, wherein the product interacts with the working electrode so as to suppress or reduce the conduction of the faradic current.

9. The method of claim 7, wherein the faradic current is induced, at least in part, by the electrochemical activity of a redox couple present in the environment adjacent the working electrode.

10. The method of claim 1, wherein:
    the first capture species includes at least two distinct capture species, each species fixed relative to the base in a spaced apart arrangement relative to the other capture species in one of a first capture region and a second capture region, and each species configured to have a binding specificity for a different analyte;
    the working electrode includes at least a first working electrode and a second working electrode, each working electrode disposed in communication with the base in a spaced apart arrangement relative to the other working electrode, and each region disposed in adjacent proximity to one of the first capture region and the second capture region respectively;
    the exposing step (b) includes exposing each of the first and second capture regions to a sample, under condition sufficient to permit binding of the each of the distinct capture species to the analyte species for which it has binding specificity, so as to immobilize the analyte species relative to the base in the event that analyte is present in the sample;
    the base is configured so that product that is produced in the first capture region substantially interacts only with the first working electrode, and product that is produced in the second capture region substantially interacts only with the second working electrode; and
    the making at least one electrical measurement step (d) includes measurement of electrochemically induced current via the first working electrode so as to detect the presence, concentration and/or amount of the corresponding analyte species is present in the sample.

11. The method of claim 3, wherein the product species interact with the working electrode so as to have one or both of the following effects so as to produce a detectable change in charge transfer:
   (i) interacts with the working electrode to produces electrochemical charge transfer; or
   (ii) interacts with the working electrode to produces inhibit charge transfer.

12. A method of detecting the presence, concentration or amount of a biomolecular analyte species in a sample using a device or assembly comprising a first capture species immobilized relative to a base, the first capture species configured to have a binding specificity for the analyte; a working electrode disposed in communication with the base, the working electrode configured to provide effective electrical communication with a communicating aqueous fluid; and a catalyst complex including a catalyst fixed to a second capture species, the second capture species configured to have a binding specificity for the analyte, and the catalyst having an activity for a selected reporter substrate to produce a product species, the product species configured to interact with the working electrode so as to produce a detectable change in an electrical property of the working electrode, the method comprising:
   (a) exposing the immobilized first capture species to analyte species present in a sample, under condition sufficient to permit binding of the first capture species to the analyte species so as to immobilize at least some of the analyte species relative to the base;
   (b) exposing the catalyst complex to the analyte species, under condition sufficient to permit binding of the second capture species to the analyte species, so as to bind the catalyst complex to at least some of the immobilized analyte species;
   (c) following carrying out in any operative order the analyte-immobilization operation (a) and the catalyst-complex-binding operation (b):
      (i) removing any unbound catalyst complex; and
      (ii) exposing the immobilized catalyst complex to the reporter substrate under condition sufficient to permit reaction of the reporter substrate with the catalyst to produce the product species; and
   (d) making at least one electrical measurement indicating the change in charge transfer due to the interaction of the product species with the working electrode so as to detect the presence, concentration and/or amount of the analyte species in the sample, wherein the working electrode comprises a nanostructured element including a material selected from the group consisting essentially of graphene monolayers and graphene multilayers, wherein the working electrode is arranged remotely from the first capture species and wherein the product is communicated to the working electrode by fluid flow.

13. The method of claim 12, wherein the analyte species comprises a polynucleotide, and wherein at least one of the first and second capture species is an oligonucleotide having a sequence complementary to a corresponding sequence of the analyte species, and the binding specificity is hybridization specificity.

14. The method of claim 12, wherein the analyte species comprises an antigen species, and wherein at least one of the first and second capture species comprises an antibody species having a binding affinity for the antigen.

15. The method of claim 12, wherein the analyte species comprises an antibody species, and wherein at least one of the first and second capture species comprises an antigen having a binding affinity for the antibody.

16. The method of claim 12, wherein the analyte species comprises a biomolecular ligand and wherein at least one of the first and second capture species comprises an biomolecular receptor having a binding specificity for the analyte species.

17. A method of detecting the presence, concentration or amount of a biomolecular analyte species in a sample using a device or assembly comprising a first capture species immobilized relative to a base, the first capture species configured to have a binding specificity for the analyte; a working electrode disposed in communication with the base, the working electrode configured to provide effective electrical communication with a communicating aqueous fluid; and a catalyst complex including a catalyst fixed to a second capture species, the second capture species configured to have a binding specificity for the analyte, and the catalyst having an activity for a selected reporter substrate to produce a product species, the product species configured to interact with the working electrode so as to produce a detectable change in an electrical property of the working electrode, the method comprising:
   (a) exposing the immobilized first capture species to analyte species present in a sample, under condition sufficient to permit binding of the first capture species to the analyte species so as to immobilize at least some of the analyte species relative to the base;
   (b) exposing the catalyst complex to the analyte species, under condition sufficient to permit binding of the second capture species to the analyte species, so as to bind the catalyst complex to at least some of the immobilized analyte species;
   (c) following carrying out in any operative order the analyte-immobilization operation (a) and the catalyst-complex-binding operation (b):
      (i) removing any unbound catalyst complex; and
      (ii) exposing the immobilized catalyst complex to the reporter substrate under condition sufficient to permit reaction of the reporter substrate with the catalyst to produce the product species; and
   (d) making at least one electrical measurement indicating the change in charge transfer due to the interaction of the product species with the working electrode so as to detect the presence, concentration and/or amount of the analyte species in the sample, wherein the working electrode comprises a nanostructured element including a material selected from the group consisting essentially of graphene monolayers and graphene multilayers, wherein the catalyst includes an enzyme having activity to react with the reporter substrate to produce the product species, and wherein the enzyme complex includes alkaline phosphatase, and the reporter substrate includes one or more of BCIP and 1-Naphthyl.

* * * * *